United States Patent
Glezer et al.

(10) Patent No.: US 11,697,840 B2
(45) Date of Patent: *Jul. 11, 2023

(54) METHOD OF DETECTING ANALYTE IN A SAMPLE WITH BINDING REAGENT, FIRST DETECTION REAGENT, AND SECOND DETECTION REAGENT

(71) Applicant: Meso Scale Technologies, LLC., Rockville, MD (US)

(72) Inventors: Eli N. Glezer, Del Mar, CA (US); John Kenten, Boyds, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 566 days.

This patent is subject to a terminal disclaimer.

(21) Appl. No.: 16/136,498

(22) Filed: Sep. 20, 2018

(65) Prior Publication Data

US 2019/0011441 A1 Jan. 10, 2019

Related U.S. Application Data

(62) Division of application No. 14/208,040, filed on Mar. 13, 2014, now Pat. No. 10,114,015.

(60) Provisional application No. 61/779,050, filed on Mar. 13, 2013.

(51) Int. Cl.
| | | |
|---|---|---|
| C12Q 1/6844 | (2018.01) | |
| G01N 33/543 | (2006.01) | |
| C12Q 1/682 | (2018.01) | |
| C12Q 1/6837 | (2018.01) | |
| C12Q 1/6848 | (2018.01) | |
| C12Q 1/6804 | (2018.01) | |
| G01N 33/542 | (2006.01) | |

(52) U.S. Cl.
CPC .......... *C12Q 1/6844* (2013.01); *C12Q 1/682* (2013.01); *C12Q 1/6804* (2013.01); *C12Q 1/6837* (2013.01); *C12Q 1/6848* (2013.01); *G01N 33/542* (2013.01); *G01N 33/54306* (2013.01); *C12Q 2531/125* (2013.01); *C12Q 2533/107* (2013.01); *G01N 2458/10* (2013.01)

(58) Field of Classification Search
None
See application file for complete search history.

(56) References Cited

U.S. PATENT DOCUMENTS

| | | |
|---|---|---|
| 3,996,345 A | 12/1976 | Ullman et al. |
| 4,342,566 A | 8/1982 | Theofilopoulos et al. |
| 4,595,661 A | 6/1986 | Cragle et al. |
| 4,988,617 A | 1/1991 | Landegren et al. |
| 5,026,653 A | 6/1991 | Lee et al. |
| 5,093,268 A | 3/1992 | Leventis et al. |
| 5,147,806 A | 9/1992 | Kamin et al. |
| 5,185,243 A | 2/1993 | Ullman et al. |
| 5,200,314 A | 4/1993 | Urdea |
| 5,238,808 A | 8/1993 | Bard et al. |
| 5,240,863 A | 8/1993 | Shibue et al. |
| 5,308,754 A | 5/1994 | Kankare et al. |
| 5,324,457 A | 6/1994 | Zhang et al. |
| 5,561,043 A | 10/1996 | Cantor et al. |
| 5,589,136 A | 12/1996 | Northrup et al. |
| 5,591,581 A | 1/1997 | Massey et al. |
| 5,597,910 A | 1/1997 | Gudibande et al. |
| 5,620,851 A | 4/1997 | Axelrod et al. |
| 5,629,156 A | 5/1997 | Goodman et al. |
| 5,629,157 A | 5/1997 | Goodman et al. |
| 5,635,347 A | 6/1997 | Link et al. |
| 5,641,623 A | 6/1997 | Axelrod et al. |
| 5,643,713 A | 7/1997 | Liang et al. |
| 5,652,107 A | 7/1997 | Lizardi et al. |
| 5,656,731 A | 8/1997 | Urdea |
| 5,660,991 A | 8/1997 | Lakowicz et al. |
| 5,665,539 A | 9/1997 | Sano et al. |
| 5,667,974 A | 9/1997 | Birkenmeyer et al. |
| 5,679,519 A | 10/1997 | Oprandy |
| 5,705,402 A | 1/1998 | Leland et al. |
| 5,714,320 A | 2/1998 | Kool |
| 5,731,147 A | 3/1998 | Bard et al. |
| 5,759,773 A | 6/1998 | Tyagi et al. |
| 5,776,672 A | 7/1998 | Hashimoto et al. |
| 5,786,141 A | 7/1998 | Bard et al. |
| 5,837,446 A | 11/1998 | Cozzette et al. |
| 5,846,485 A | 12/1998 | Leland et al. |
| 5,854,033 A | 12/1998 | Lizardi |
| 5,866,434 A | 2/1999 | Massey et al. |
| 5,871,921 A | 2/1999 | Landegren et al. |

(Continued)

FOREIGN PATENT DOCUMENTS

| | | |
|---|---|---|
| CN | 1446050 A | 10/2003 |
| CN | 101198707 A | 6/2008 |

(Continued)

OTHER PUBLICATIONS

He, X. Development of on-chip proximity ligation assay with in situ single molecule sequencing readout. Masters Dissertation, Uppsala University. (Year: 2011).*
European Examination Report dated Jan. 24, 2019 received in European Patent Application No. 14 774 276.1.
Australian Examination Report dated Aug. 23, 2018 received in Australian Patent Application No. 2014244010.
Final Office Action in U.S. Appl. No. 15/440,191, dated May 22, 2020.
Andras S.C. et al., "Strategies for Signal Amplification in Nucleic Acid Detection", Molecular Biotechnology 19:29-44 (2001).
Baner J. et al., "Signal Amplification of Padlock Probes by Rolling Circle Replication", Nucleic Acids Research 26(22):15073-5078 (1998).

(Continued)

*Primary Examiner* — Samuel C Woolwine
(74) *Attorney, Agent, or Firm* — Medler Ferro Woodhouse & Mills

(57) ABSTRACT

The present invention is directed to improved methods for conducting immunoassays. The methods are designed to amplify signals in immunoassays and anchor immunoassay complexes employed therein.

27 Claims, 11 Drawing Sheets

Specification includes a Sequence Listing.

(56) References Cited

U.S. PATENT DOCUMENTS

| | | |
|---|---|---|
| 5,942,391 A | 8/1999 | Zhang et al. |
| 6,054,274 A | 4/2000 | Sampson et al. |
| 6,066,448 A | 5/2000 | Wohlstadter et al. |
| 6,077,668 A | 6/2000 | Kool |
| 6,136,268 A | 10/2000 | Ala-Kleme et al. |
| 6,140,135 A | 10/2000 | Landegren et al. |
| 6,143,495 A | 11/2000 | Lizardi et al. |
| 6,183,960 B1 | 2/2001 | Lizardi |
| 6,207,369 B1 | 3/2001 | Wohlstadter et al. |
| 6,210,884 B1 | 4/2001 | Lizardi |
| 6,214,552 B1 | 4/2001 | Heroux et al. |
| 6,235,472 B1 | 5/2001 | Landegren et al. |
| 6,287,824 B1 | 9/2001 | Lizardi |
| 6,291,187 B1 | 9/2001 | Kingsmore et al. |
| 6,316,229 B1 | 11/2001 | Lizardi et al. |
| 6,323,009 B1 | 11/2001 | Lasken et al. |
| 6,329,150 B1 | 12/2001 | Lizardi et al. |
| 6,344,329 B1 | 2/2002 | Lizardi |
| 6,368,801 B1 | 4/2002 | Faruqi |
| 6,511,809 B2 | 1/2003 | Baez et al. |
| 6,531,283 B1 | 3/2003 | Kingsmore et al. |
| 6,558,928 B1 | 5/2003 | Landegren |
| 6,569,647 B1 | 5/2003 | Zhang et al. |
| 6,632,609 B2 | 10/2003 | Lizardi |
| 6,646,118 B2 | 11/2003 | Kwiatkowski et al. |
| 6,673,533 B1 | 1/2004 | Wohlstadter et al. |
| RE38,442 E | 2/2004 | Zhang et al. |
| 6,709,815 B1 | 3/2004 | Dong et al. |
| 6,797,474 B2 | 9/2004 | Lizardi |
| 6,878,515 B1 | 4/2005 | Landegren |
| 6,939,720 B2 | 9/2005 | Chandler et al. |
| 6,977,722 B2 | 12/2005 | Wohlstadter et al. |
| 7,074,564 B2 | 7/2006 | Landegren |
| 7,192,703 B2 | 3/2007 | Sun et al. |
| 7,306,904 B2 | 12/2007 | Landegren et al. |
| 7,320,860 B2 | 1/2008 | Landegren et al. |
| 7,351,528 B2 | 4/2008 | Landegren |
| 7,618,776 B2 | 11/2009 | Lizardi |
| 7,790,388 B2 | 9/2010 | Landegren et al. |
| 7,842,246 B2 | 11/2010 | Wohlstadter et al. |
| 7,883,848 B2 | 2/2011 | Ericsson |
| 7,883,849 B1 | 2/2011 | Dahl |
| 7,932,060 B2 | 4/2011 | Nadeau et al. |
| 8,013,134 B2 | 9/2011 | Fredriksson |
| 8,053,188 B2 | 11/2011 | Gullberg et al. |
| 8,080,393 B2 | 12/2011 | Koch et al. |
| 8,163,499 B2 | 4/2012 | Singh et al. |
| 8,222,047 B2 | 7/2012 | Duffy et al. |
| 8,236,574 B2 | 8/2012 | Duffy et al. |
| 8,268,554 B2 | 9/2012 | Schallmeiner |
| 8,338,776 B2 | 12/2012 | Walt et al. |
| 8,741,559 B2 | 6/2014 | Treiber et al. |
| 9,618,510 B2 | 4/2017 | Aghvanyan et al. |
| 9,777,338 B2 | 10/2017 | Glezer et al. |
| 10,114,015 B2 | 10/2018 | Glezer et al. |
| 10,408,823 B2 | 9/2019 | Aghvanyan et al. |
| 10,908,157 B2 | 2/2021 | Aghvanyan et al. |
| 11,242,570 B2 | 2/2022 | Glezer |
| 2002/0035247 A1 | 3/2002 | Kwiatkowski et al. |
| 2002/0051986 A1 | 5/2002 | Baez et al. |
| 2002/0064779 A1 | 5/2002 | Landegren et al. |
| 2002/0102592 A1 | 8/2002 | Landegren |
| 2002/0155490 A1 | 10/2002 | Skinner et al. |
| 2003/0077670 A1 | 4/2003 | Cheng et al. |
| 2004/0023271 A1 | 2/2004 | Kurn et al. |
| 2004/0121382 A1 | 6/2004 | Liu et al. |
| 2004/0142323 A1 | 7/2004 | Boyde |
| 2004/0209261 A1 | 10/2004 | Keys et al. |
| 2004/0248103 A1 | 12/2004 | Feaver et al. |
| 2004/0265897 A1 | 12/2004 | Lizardi |
| 2005/0003432 A1 | 1/2005 | Hall et al. |
| 2005/0009050 A1 * | 1/2005 | Nadeau .......... C12Q 1/6804 435/6.18 |
| 2005/0014140 A1 | 1/2005 | Erikson et al. |
| 2005/0282158 A1 | 12/2005 | Landegren |
| 2005/0287526 A1 | 12/2005 | Landegren et al. |
| 2007/0161029 A1 | 7/2007 | Li et al. |
| 2007/0259381 A1 | 11/2007 | Rissin et al. |
| 2007/0259385 A1 | 11/2007 | Rissin et al. |
| 2007/0259448 A1 | 11/2007 | Rissin et al. |
| 2008/0188638 A1 | 8/2008 | Breitenkamp et al. |
| 2009/0176318 A1 | 7/2009 | Kolpashchikov |
| 2009/0178934 A1 | 7/2009 | Jarvius et al. |
| 2009/0203155 A1 | 8/2009 | Chiku |
| 2010/0075862 A1 | 3/2010 | Duffy et al. |
| 2010/0129819 A1 | 5/2010 | Hu et al. |
| 2010/0261292 A1 | 10/2010 | Glezer et al. |
| 2011/0177054 A1 | 7/2011 | Gibbings et al. |
| 2011/0212537 A1 | 9/2011 | Rissin et al. |
| 2012/0196774 A1 | 8/2012 | Fournier et al. |
| 2012/0252692 A1 | 10/2012 | Kutyavin |
| 2012/0289428 A1 | 11/2012 | Duffy et al. |
| 2013/0059741 A1 | 3/2013 | Weiner |
| 2013/0323756 A1 | 12/2013 | Tullis et al. |
| 2014/0194311 A1 | 7/2014 | Gullberg et al. |
| 2014/0272939 A1 | 9/2014 | Aghvanyan et al. |
| 2014/0274775 A1 | 9/2014 | Glezer et al. |
| 2014/0315189 A1 | 10/2014 | Glezer et al. |
| 2015/0044674 A1 | 2/2015 | Fredriksson et al. |
| 2017/0089892 A1 | 3/2017 | Aghvanyan et al. |
| 2017/0168047 A1 | 6/2017 | Aghvanyan et al. |
| 2017/0362668 A1 | 12/2017 | Glezer et al. |
| 2019/0011441 A1 | 1/2019 | Glezer et al. |
| 2019/0391140 A1 | 12/2019 | Aghvanyan et al. |
| 2021/0190778 A1 | 6/2021 | Aghvanyan et al. |
| 2022/0033918 A1 | 2/2022 | Glezer |

FOREIGN PATENT DOCUMENTS

| | | |
|---|---|---|
| CN | 101988920 A | 3/2011 |
| CN | 102317779 A | 1/2012 |
| CN | 103703145 B | 4/2014 |
| CN | 104114718 A | 10/2014 |
| CN | 108374052 A | 8/2018 |
| EP | 1 985 714 A1 | 10/2008 |
| EP | 2 500 435 A1 | 9/2012 |
| JP | 4-262799 | 9/1992 |
| JP | H08-505050 A | 6/1996 |
| JP | 11-508040 | 7/1999 |
| JP | 2005-521409 A | 7/2005 |
| JP | 2006-511807 A | 4/2006 |
| JP | 2007-525661 A | 9/2007 |
| JP | 2009-106220 A | 5/2009 |
| JP | 2009-222712 A | 10/2009 |
| WO | 90/05910 A1 | 5/1990 |
| WO | 91/17442 A1 | 11/1991 |
| WO | 94/14961 A1 | 7/1994 |
| WO | 95/35390 A1 | 12/1995 |
| WO | 97/36931 A1 | 10/1997 |
| WO | 98/12539 A1 | 3/1998 |
| WO | 98/57154 A1 | 12/1998 |
| WO | 99/14599 A1 | 3/1999 |
| WO | 99/32662 A1 | 7/1999 |
| WO | 99/49079 A1 | 9/1999 |
| WO | 99/58962 A1 | 11/1999 |
| WO | 99/63347 A2 | 12/1999 |
| WO | 00/03233 A1 | 1/2000 |
| WO | 00/04193 A1 | 1/2000 |
| WO | 01/35100 A2 | 5/2001 |
| WO | 01/84146 A2 | 11/2001 |
| WO | 03/033722 A2 | 4/2003 |
| WO | 2004/061131 A1 | 7/2004 |
| WO | 2004/094456 A2 | 11/2004 |
| WO | 2005/059509 A2 | 6/2005 |
| WO | 2009/029073 A1 | 3/2009 |
| WO | 2009/067009 A1 | 5/2009 |
| WO | 2009/092386 A2 | 7/2009 |
| WO | 2010/059820 A1 | 5/2010 |
| WO | 2011/047087 A2 | 4/2011 |
| WO | 2011/143583 A1 | 11/2011 |
| WO | 2012/007511 A1 | 2/2012 |
| WO | 2012/049316 A1 | 4/2012 |
| WO | 2012/104261 A1 | 8/2012 |
| WO | 2012/152942 A1 | 11/2012 |

(56) References Cited

FOREIGN PATENT DOCUMENTS

| | | |
|---|---|---|
| WO | 2012/160083 A1 | 11/2012 |
| WO | 2013/113699 A2 | 8/2013 |
| WO | 2014/031984 A1 | 2/2014 |
| WO | 2014/160192 A1 | 10/2014 |
| WO | 2014/165061 A1 | 10/2014 |
| WO | 2015/175856 A1 | 11/2015 |
| WO | 2022/051485 A2 | 3/2022 |

OTHER PUBLICATIONS

Dahl F. et al., "Circle-to-Circle Amplification for Precise and Sensitive DNA Analysis", PNAS 101(13):14548-4553 (Mar. 30, 2004).

Darmanis S. et al., "Self-Assembly of Proximity Probes for Flexible and Modular Proximity Ligation Assays", BioTechniques 46(4):1443-450 (Oct. 2007).

Dean F.B. et al., "Rapid Amplification of Plasmid and Phage DNA Using Phi29 DNA Polymerase and Multiply-Primed Rolling Circle Amplification", Genome Research 1095-1099 (2001).

Ericsson O. et al., "A Dual-Tag Microarray Platform for High-Performance Nucleic Acid and Protein Analyses", Nucleic Acids Research 36(8):e45 (9 pages) (2008).

Faruqi F.A. et al., "High-Throughput Genotyping of Single Nucleotide Polymorphisms With Rolling Circle Amplification", BMC Genomics 2(4) (10 pages) (2001).

Fire A. et al., "Rolling Replication of Short DNA Circles", Proc. Natl. Acad. Sci. USA 92:4641-4645 (May 1995).

Fredriksson S. et al., "Multiplexed Protein Detection by Proximity Ligation for Cancer Biomarker Validation", Nature Methods 4(4):327-329 (Apr. 2007).

Fredriksson S. et al., "Protein Detection Using Proximity-Dependent DNA Ligation Assays", Nature Biotechnology 20:473-477 (May 2002).

Gajadhar A. et al., "A Proximity Ligation Assay Using Transiently Transfected, Epitope-Tagged Proteins: Application for In Situ Detection of Dimerized Receptor Tyrosine Kinases", 48(2):145-151 (2010).

Gill P. et al., "Nucleic Acid Isothermal Amplification Technologies—A Review", Nucleosides, Nucleotides, and Nucleic Acids 27:224-243 (2008).

Griffiths A.D. et al., "Miniaturising the Laboratory in Emulsion Droplets", Trends in Biotechnology 24(9):395-402 (2006).

Gullberg M. et al., "A Sense of Closeness: Protein Detection by Proximity Ligation", Current Opinion in Biotechnology 14:82-86 (2003).

Gustafsdottir S.M. et al., "Detection of Individual Microbial Pathogens by Proximity Ligation", Clinical Chemistry 52(6):1152-1160 (2006).

Hochman J. et al., "An Active Antibody Fragment (Fv) Composed of the Variable Portions of Heavy and Light Chains", Biochemistry 12(6):1130-1135 (1973).

Holder P.K. et al., "Assignment of Neisseria Meningitidis Serogroup A and C Class-Specific Anticapsular Antibody Concentrations to the New Standard Reference Serum CDC1992", Clinical and Diagnostic Laboratory Immunology 2(2):132-137 (Mar. 1995).

Jeong Y-J et al., "Isothermal DNA Amplification In Vitro: The Helicase-Dependent Amplification System", Cellular and Molecular Life Sciences 66:3325-3336 (2009).

Landegren U. et al., "A Ligase-Mediated Gene Detection Technique", Science 241:1077:1080 (Aug. 26, 1988).

Leuchowius K-J et al., "Parallel Visualization of Multiple Protein Complexes in Individual Cells in Tumor Tissue", Molecular & Cellular Proteomics 12:1563-1571 (2013).

Lizardi P.M. et al., "Mutation Detection and Single-Molecule Counting Using Isothermal Rolling-Circle Amplification", Nature Genetics 19:225-232 (Jul. 1998).

Marchese R.D. et al., "Optimization and Validation of a Multiplex, Electrochemiluminescence-Based Detection Assay for the Quantitation of Immunoglobulin G Serotype-Specific Antipneumococcal Antibodies in Human Serum", Clinical and Vaccine Immunology 16(3):387-396 (Mar. 2009).

Mendoza L.G. et al., "High-Throughput Microarray-Based Enzyme-Linked Immunosorbent Assay (ELISA)", BioTechniques 27(4):778-788 (Oct. 1999).

Nallur G. et al., "Signal Amplification by Rolling Circle Amplification on DNA Microarrays", Nucleic Acids Research 29(23):e118 (9 pages) (2001).

Nilsson M. et al., "Padlock Probes: Circularizing Oligonucleotides for Localized DNA Detection", Science 265:2085-2088 (Sep. 30, 1994).

Nolan J.P. et al., "Multiplexed and Microparticle-Based Analyses: Quantitative Tools for the Large-Scale Analysis of Biological Systems", Cytometry Part A 69A:318-325 (2006).

Nordengrahn A. et al., "Evaluation of a Novel Proximity Ligation Assay for the Sensitive and Rapid Detection of Foot-and-Mouth Disease Virus", Veterinary Microbiology 127:227-236 (2008).

Porter R.R. et al., "Subunits of Immunoglobulins and Their Relationship to Antibody Specificity", J. Cell Physiol. 67(Sup 1):51-64 (1966).

Samiotaki M. et al., "Dual-Color Detection of DNA Sequence Variants by Ligase-Mediated Analysis", Genomics 20:238-242 (1994).

Schallmeiner E. et al., "Sensitive Protein Detection via Triple-Binder Proximity Ligation Assays", Nature Methods 4(2):135-137 (Feb. 2007).

Schweitzer B. et al., "Multiplexed Protein Profiling on Microarrays by Rolling-Circle Amplification", Nature Biotechnology 20:359-365 (Apr. 2002).

Schweitzer B. et al., "Immunoassays With Rolling Circle DNA Amplification: A Versatile Platform for Ultrasensitive Antigen Detection", PNAS 97(18):10113-10119 (Aug. 29, 2000).

Soderberg O. et al., "Characterizing Proteins and Their Interactions in Cells and Tissues Using the In Situ Proximity Ligation Assay", Methods 45:227-232 (2008).

Spits C. et al., "Whole-Genome Multiple Displacement Amplification from Single Cells", Nature Protocols 1(4):1965-1970 (2006).

Vincent M. et al., "Helicase-Dependent Isothermal DNA Amplification", European Molecular Biology Organization 5(8):795-800 (2004).

Vuoriluoto M. et al., "Spatio-Temporal Composition of the Mitotic Chromosomal Passenger Complex Detected Using In Situ Proximity Ligation Assay", Molecular Oncology 5:105-111 (2011).

Weibrecht I. et al., "Proximity Ligation Assays: A Recent Addition to the Proteomics Toolbox", Expert Rev. Proteomics 7(3):401-409 (2010).

Zhang D. et al., "Amplification of Circularizable Probes for the Detection of Target Nucleic Acids and Proteins", Clinica Chimica Acta 363:61-70 (2006).

Zhou H. et al., "Two-Color, Rolling-Circle Amplification on Antibody Microarrays for Sensitive, Multiplexed Serum-Protein Measurements", Genome Biology 5:R28 (12 pages) (2008).

Yamada K. et al., "Detection of Methicillin-Resistant *Staphylococcus aureus* Using a Specific Anti-PBP2a Chicken IgY Antibody", Jpn. J. Infect. Dis. 66:103-108 (2013).

Duolink II Probemaker Plus, Duolink II Probemaker Minus, Product Insert Doc No. 0564, OLINK Bioscience.

Supplementary Table 2 to Fredriksson S. et al., "Multiplexed Protein Detection by Proximity Ligation for Cancer Biomarker Validation", Nature Methods 4(4):327-329 (Apr. 2007).

Meso Scale Discovery Inc: "Sandwhich Immunogenicity Assays for Protein Drugs", Meso Scale Discovery, Inc. Rockville, Maryland USA, (1 page) (Nov. 1, 2012).

Chinese Office Action dated Jul. 4, 2017 received in Chinese Patent Application No. 201480026027.6, together with an English-language translation.

Chinese Office Action dated Oct. 28, 2016 received in Chinese Patent Application No. 201480026027.6, together with an English-language translation.

English-language Translation of Chinese Office Action dated Aug. 20, 2018 received in Chinese Patent Application No. 201480025989.X.

(56) References Cited

OTHER PUBLICATIONS

English-language Translation of Chinese Office Action dated Dec. 1, 2017 received in Chinese Patent Application No. 201480025989.X.
English-language Translation of Chinese Office Action dated Feb. 28, 2017 received in Chinese Patent Application No. 201480025989.X.
Japanese Notice of Reasons for Rejection dated Feb. 27, 2018 received in Japanese Patent Application No. 2016-501461, together with an English-language translation.
International Search Report and Written Opinion dated Jul. 7, 2014 received from the International Searching Authority received in International Application No. PCT/US2014/026010.
International Search Report and Written Opinion dated Jul. 17, 2014 received from the International Searching Authority received in International Application No. PCT/US2014/024279.
European Examination Report dated Oct. 19, 2017 received in European Patent Application No. 14 774 276.1.
European Communication dated Jun. 21, 2017 received in European Patent Application No. 14 779 523.1.
Extended Supplementary European Search Report dated Sep. 26, 2016 received in European Patent Application No. 14 77 9523.1.
Extended Supplementary European Search Report dated Jul. 27, 2016 received in European Patent Application No. 14 774 276.1.
U.S. non-Final Office Action dated Jan. 16, 2018 received in U.S. Appl. No. 14/208,040.
U.S. Final Office Action dated Jul. 27, 2017 received in U.S. Appl. No. 14/208,040.
U.S. non-Final Office Action dated Feb. 7, 2017 received in U.S. Appl. No. 14/208,040.
U.S. Final Office Action dated Oct. 11, 2016 received in U.S. Appl. No. 14/208,040.
U.S. non-Final Office Action dated Dec. 30, 2015 received in U.S. Appl. No. 14/208,040.
Darmanis et al., "Sensitive Plasma Protein Analysis by Microparticle-Based Proximity Ligation Assays," Mol. Cell Proteomics, 9(2): 327-335 (2010).
Nong et al., "Solid-phase Proximity Ligation Assays for Individual or Parallel Protein Analyses with Readout via Real-Time PCR or Sequencing," Nat. Protocols, 8(6): 1234-1248(2013).
Non-final Office Action issued in U.S. Appl. No. 15/440,191, dated Jun. 20, 2019.
Final Office Action issued in U.S. Appl. No. 15/440,191, dated Dec. 16, 2019.
Non-final Office Action issued in U.S. Appl. No. 15/311,309, dated May 4, 2018.
Final Office Action issued in U.S. Appl. No. 15/311,309, dated Oct. 26, 2018.
International Search Report issued in related PCT/US15/30925, dated Aug. 27, 2015.
U.S. Final Office Action dated Jul. 6, 2016 received in U.S. Appl. No. 14/206,284.
U.S. non-Final Office Action dated Oct. 16, 2015 received in U.S. Appl. No. 14/206,284.
Adler et al., "Detection of rViscumin in plasma samples by immuno-PCR," Biochemical and Biophysical Research Communications 300:757-763 (2003).
Chan, "General principle of immunoassay." Immunoassay: A Practical Guide; pp. 1-23 (1987).
Darmanis et al., "ProteinSeq: High-Performance Proteomic Analyses by Proximity Ligation and Next Generation Sequencing," PLOS One 6(9) p.e25583 (2011).
Heyduk et al., "Molecular Pincers: Antibody-Based Homogeneous Protein Sensors," Analytical Chemistry 80(13):5152-5159 (2008).
Hu et al., "Quantitation of Femtomolar Protein Levels via Direct Readout With the Electrochemical Proximity Assay," Journal of the American Chemical Society 134(16): 7066-7072 (2012).
Niemeyer et al., "Fluorometric Polymerase Chain Reaction (PCR) Enzyme-Linked Immunosorbent Assay for Quantification of Immuno-PCR Products in Microplates," Analytical Biochemistry 246:140-145 (1997).
Tavoosidana et al. "Multiple Recognition Assay Reveals Prostasomes as Promising Plasma Biomarkers for Prostate Cancer," PNAS 108(21):8809-8814 (2011).
International Search Report issued in PCT/US2012/064263, dated Mar. 15, 2013.
Restriction Requirement in U.S. Appl. No. 16/564,208, dated Nov. 10, 2020.
Non-Final Office Action in U.S. Appl. No. 16/564,208, dated May 10, 2021.
Final Office Action in U.S. Appl. No. 16/564,208, dated Oct. 6, 2021.
Restriction Requirement in U.S. Appl. No. 14/357,653, dated Jul. 31, 2015.
Non-Final Office Action in U.S. Appl. No. 14/357,653, dated Oct. 26, 2015.
Final Office Action in U.S. Appl. No. 14/357,653, dated Jun. 22, 2016.
Non-Final Office Action in U.S. Appl. No. 14/357,653, dated Jan. 31, 2017.
Non-Final Office Action in U.S. Appl. No. 15/696,953, dated Mar. 27, 2019.
Final Office Action in U.S. Appl. No. 15/696,953, dated Nov. 25, 2019.
Final Office Action in U.S. Appl. No. 15/696,953, dated Jun. 15, 2020.
Non-Final Office Action in U.S. Appl. No. 15/696,953, dated Mar. 9, 2021.
Notice of Allowance in U.S. Appl. No. 15/696,953, dated Sep. 27, 2021.
Soderberg et al., "Direct observation of individual endogenous protein complexes in situ by proximity ligation," Nature Methods 3(12):995-1000 (2006).
Notice of Allowance issued in U.S. Appl. No. 15/311,309, dated May 9, 2019.
Advisory Action issued in U.S. Appl. No. 16/564,208, dated Jan. 27, 2022.
Notice of Allowance in U.S. Appl. No. 16/564,208, dated Apr. 25, 2022.
Supplemental Notice of Allowance in U.S. Appl. No. 16/564,208, dated May 18, 2022.
Lee et al., "Diffractometric Detection of Proteins using Microbead-based Rolling Circle Amplification," Analytical Chemistry 82(1):197 (2010).
Supplemental Notice of Allowance in U.S. Appl. No. 16/564,208, dated Jul. 21, 2022.
Supplemental Notice of Allowance in U.S. Appl. No. 16/564,208, dated Aug. 17, 2022.
Break et al., "Utilization of the N-PLEX™ Platform for the Detectin of Antisense Oligonucleotides (ASOs) in Plasma," Molecular Therapy; 2020 ASGCT Annual Meeting Abstracts, 28(4-S1):549 (Apr. 28, 2020).
Non-Final Office Action in U.S. Appl. No. 17/504,937, dated Apr. 17, 2023.

* cited by examiner

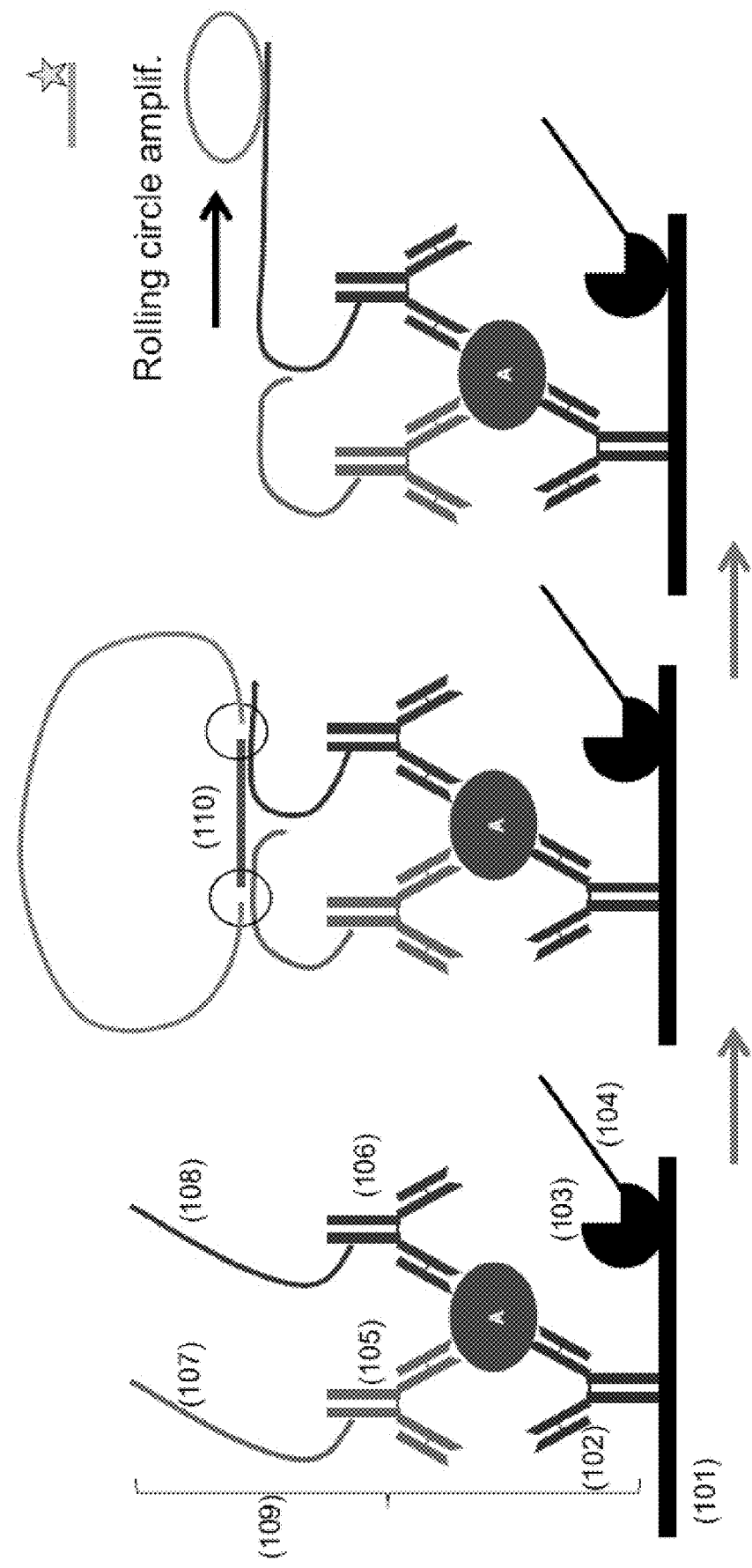

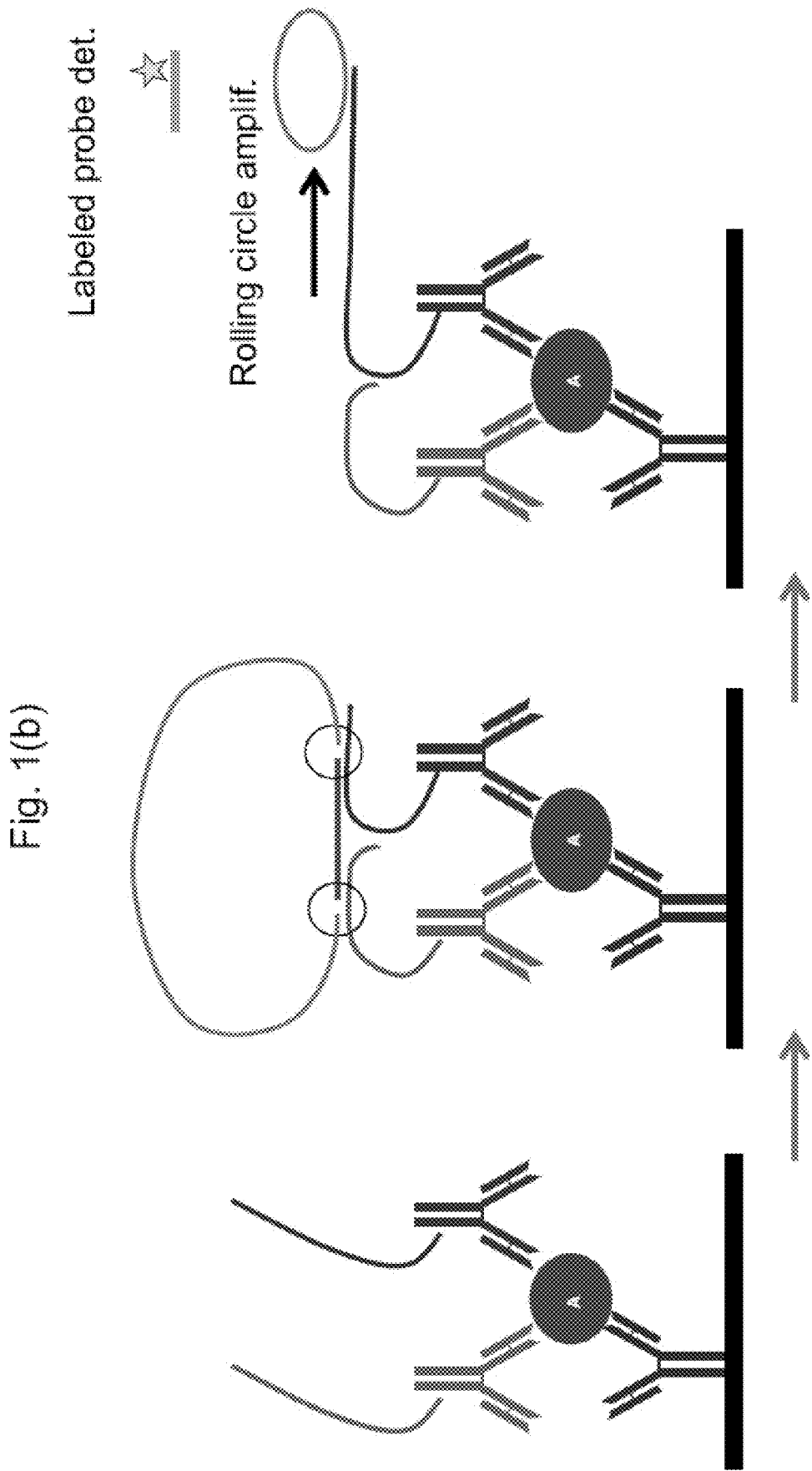

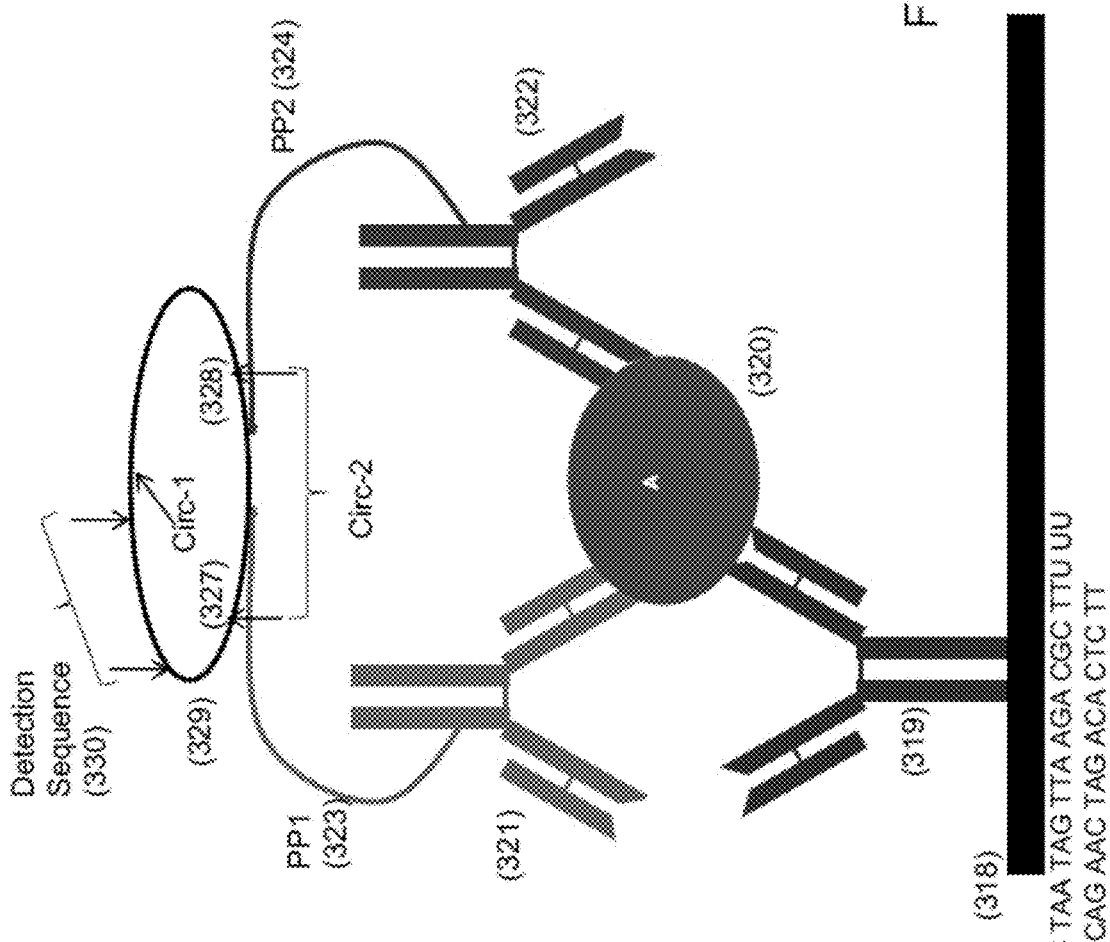

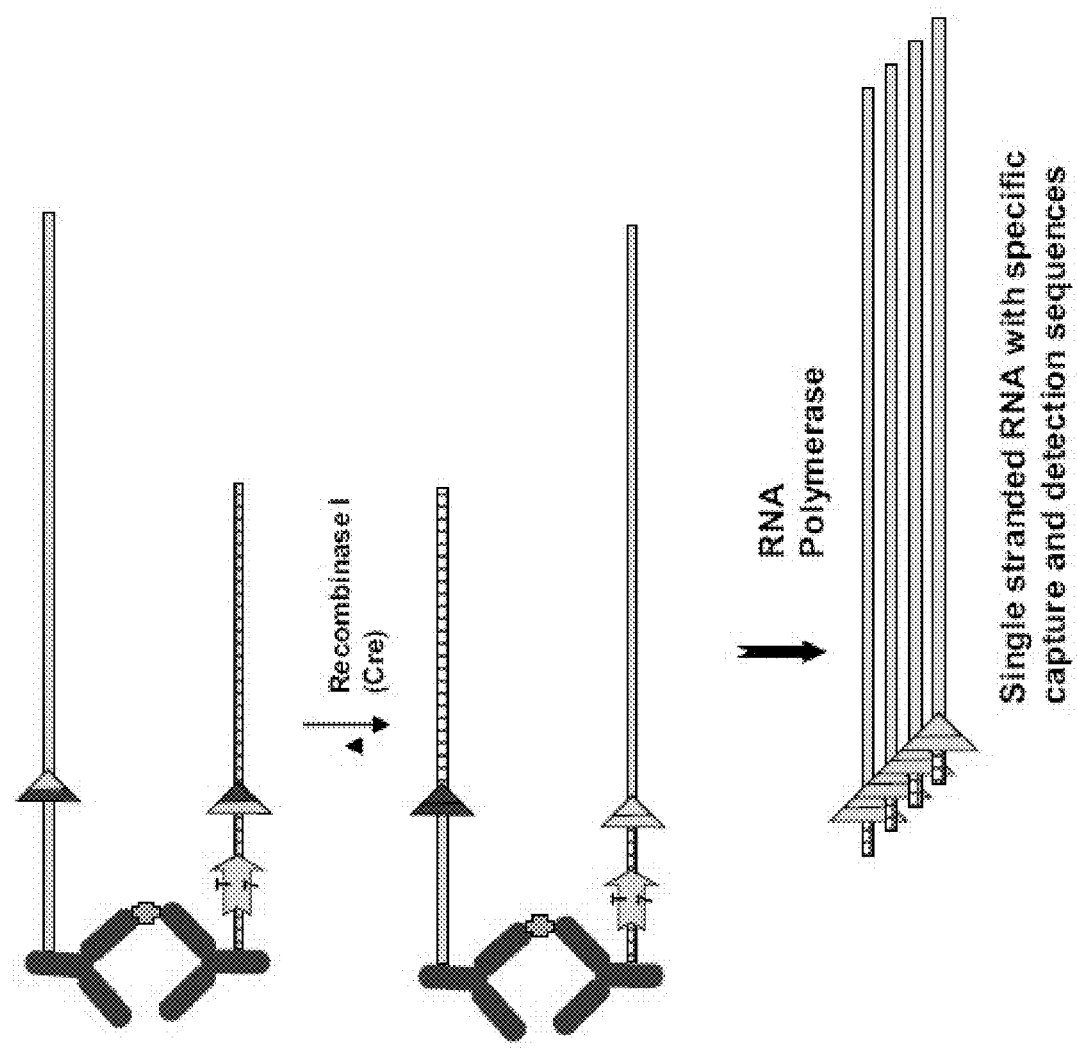

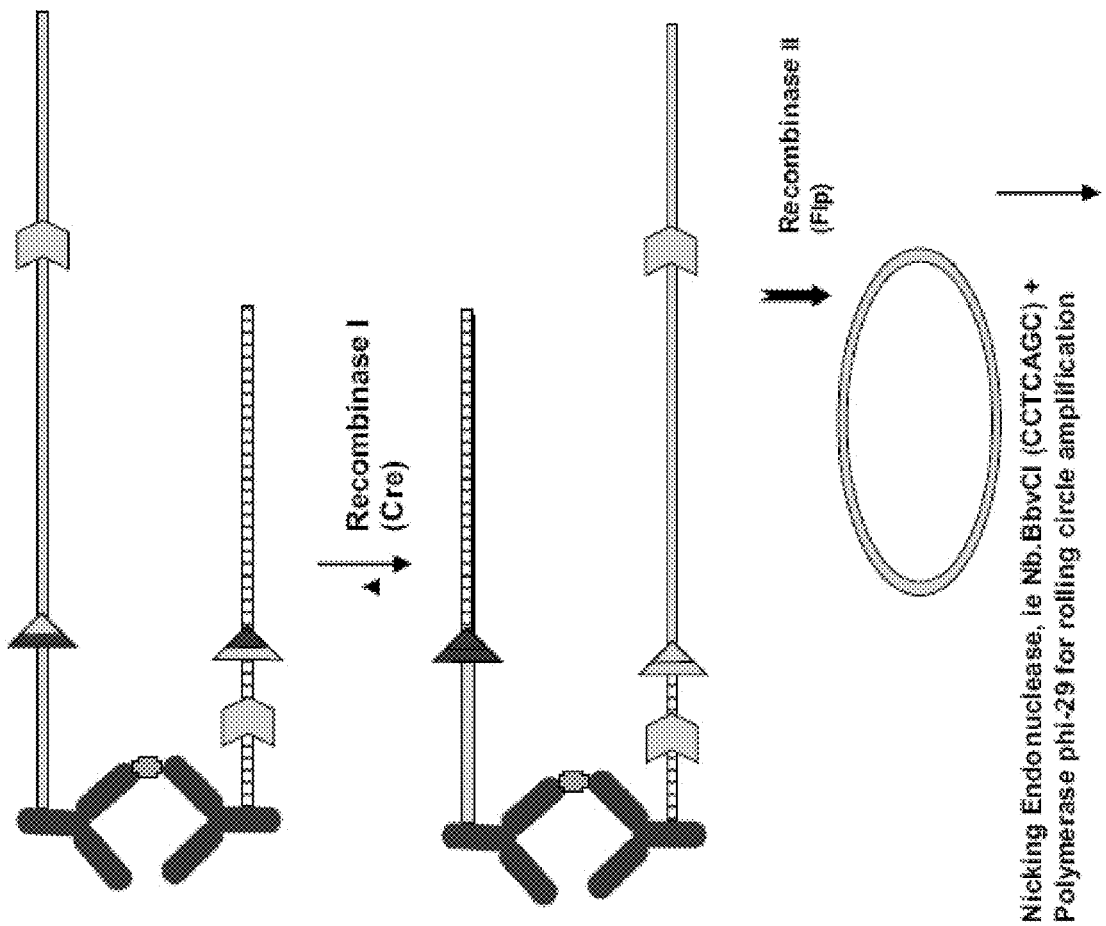

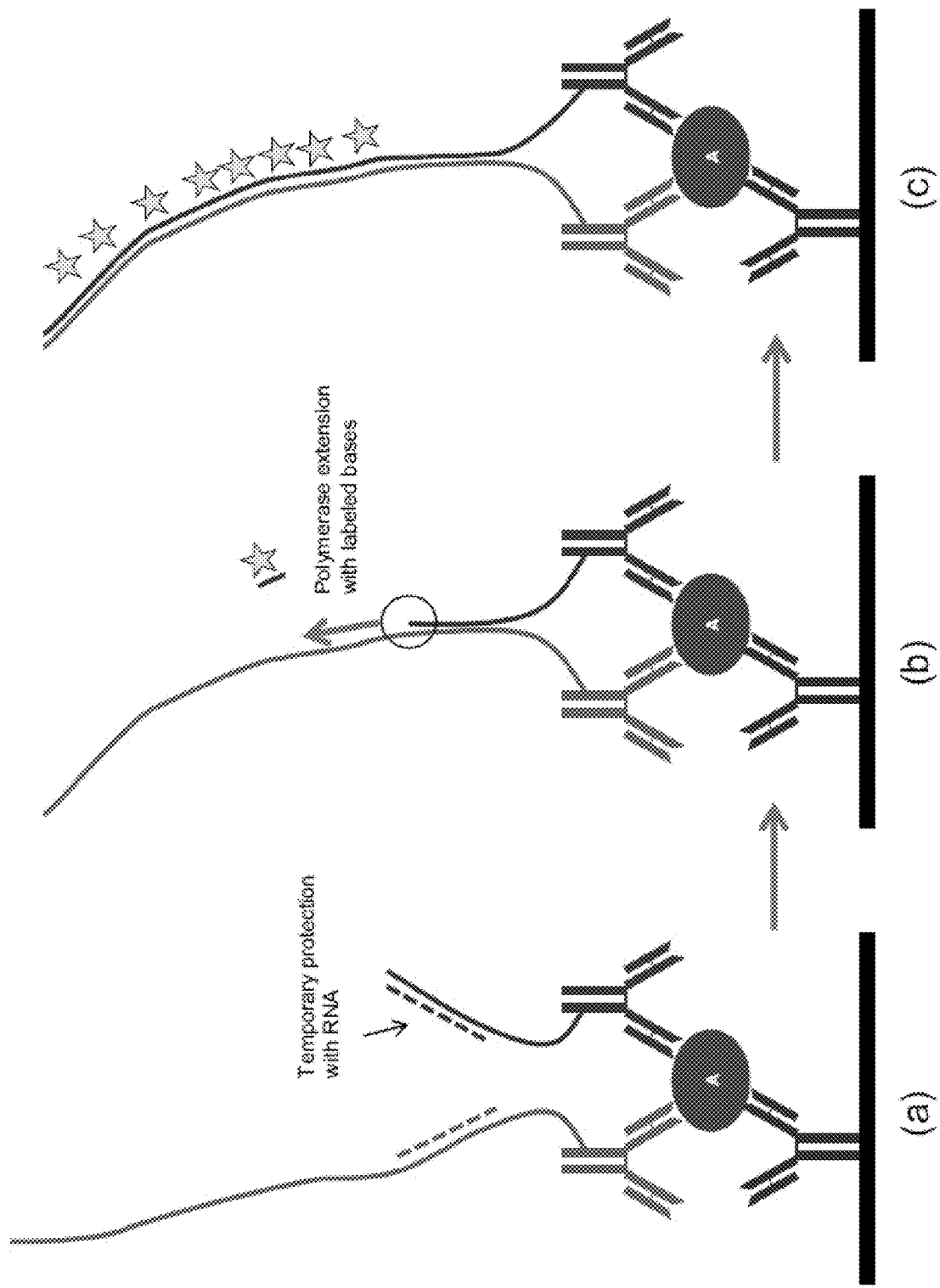

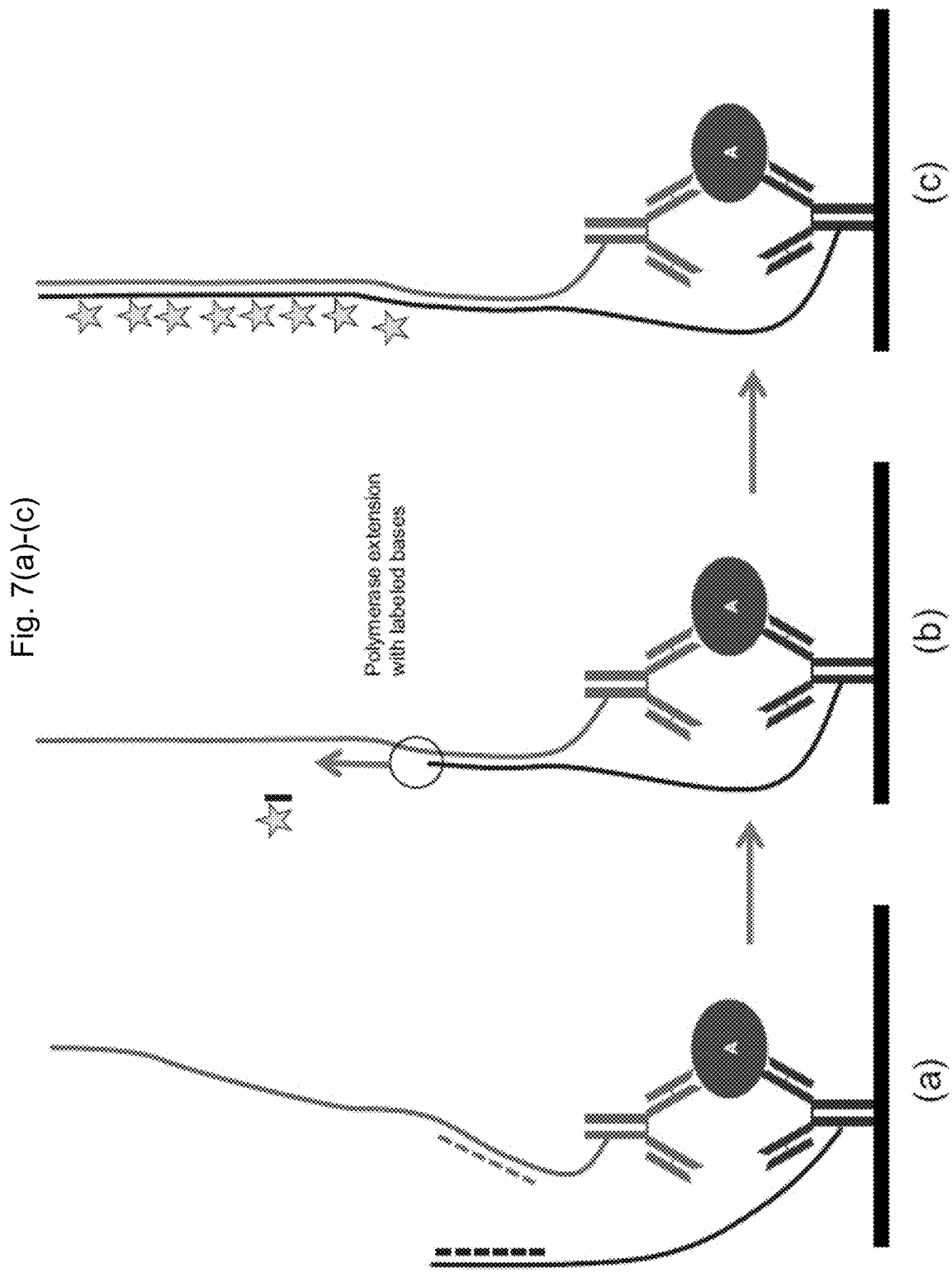

SEQUENCE LISTING

```
<160> NUMBER OF SEQ ID NOS: 5

<210> SEQ ID NO 1
<211> LENGTH: 35
<212> TYPE: DNA
<213> ORGANISM: Artificial Sequence
<220> FEATURE:
<223> OTHER INFORMATION: Thiol-modified proximity probe 1
<220> FEATURE:
<221> NAME/KEY: modified_base
<222> LOCATION: (33)..(35)
<223> OTHER INFORMATION: um

<400> SEQUENCE: 1
aaaaaaaaaa gacgctaata gttaagacgc ttuuu                           35

<210> SEQ ID NO 2
<211> LENGTH: 32
<212> TYPE: DNA
<213> ORGANISM: Artificial Sequence
<220> FEATURE:
<223> OTHER INFORMATION: Thiol-modified proximity probe 2

<400> SEQUENCE: 2
aaaaaaaaaa tatgacagaa ctagacactc tt                              32

<210> SEQ ID NO 3
<211> LENGTH: 65
<212> TYPE: DNA
<213> ORGANISM: Artificial Sequence
<220> FEATURE:
<223> OTHER INFORMATION: Circularization oligonucleotide 1

<400> SEQUENCE: 3
ctattagcgt ccagtgaatg cgagtccgtc taagagagta gtagagcagc cgtcaagagt    60
gtcta                                                               65

<210> SEQ ID NO 4
<211> LENGTH: 25
<212> TYPE: DNA
<213> ORGANISM: Artificial Sequence
<220> FEATURE:
<223> OTHER INFORMATION: Circularization oligonucletide 2

<400> SEQUENCE: 4
gttctgtcat atttaagcgt cttaa                                      25

<210> SEQ ID NO 5
<211> LENGTH: 20
<212> TYPE: DNA
<213> ORGANISM: Artificial Sequence
<220> FEATURE:
<223> OTHER INFORMATION: Detection probe

<400> SEQUENCE: 5
cagtgaatgc gagtccgtct                                            20
```

METHOD OF DETECTING ANALYTE IN A SAMPLE WITH BINDING REAGENT, FIRST DETECTION REAGENT, AND SECOND DETECTION REAGENT

CROSS REFERENCE TO RELATED APPLICATIONS

The present application is a divisional of co-pending application having U.S. Ser. No. 14/208,040, filed on Mar. 13, 2014, which claims benefit of U.S. Provisional Application No. 61/779,050, filed on Mar. 13, 2013, the disclosure of which is incorporated herein by reference in its entirety.

INCORPORATION BY REFERENCE OF SEQUENCE LISTING

The Sequence Listing in the ASCII text file, named as 29901_sequencelisting.txt of 2 KB, created on Mar. 12, 2014, and submitted to the United States Patent and Trademark Office via EFS-Web, is incorporated herein by reference.

REFERENCE FIELD OF THE INVENTION

The present invention is directed to improved methods for conducting immunoassays. The methods are designed to amplify signals in immunoassays and anchor immunoassay complexes employed therein.

BACKGROUND OF THE INVENTION

A substantial body of literature has been developed concerning techniques that employ binding reactions, e.g., antigen-antibody reactions, nucleic acid hybridization and receptor-ligand reactions, for the sensitive measurement of analytes of interest in samples. The high degree of specificity in many biochemical binding systems has led to many assay methods and systems of value in a variety of markets including basic research, human and veterinary diagnostics, environmental monitoring and industrial testing. The presence of an analyte of interest may be measured by directly measuring the participation of the analyte in a binding reaction. In some approaches, this participation may be indicated through the measurement of an observable label attached to one or more of the binding materials.

While the sandwich immunoassay format provides excellent sensitivity and specificity in many applications, some analytes are present at concentrations that are too low for detection by conventional immunoassay techniques. The performance of sandwich immunoassays can also be limited by the non-specific binding of detection antibodies and by the instability of sandwich complexes comprising high off-rate antibodies. There is a need for new techniques for improving sandwich immunoassay performance by improving sensitivity, reducing non-specific binding and improving the stability of sandwich complexes.

SUMMARY OF THE INVENTION

The invention provides a method of detecting an analyte of interest in a sample comprising: (a) contacting the sample with a surface comprising (i) a binding reagent for the analyte, and (ii) an anchoring reagent comprising an anchoring oligonucleotide sequence complementary to an amplicon sequence, and binding the analyte to the binding reagent to form a surface-bound complex; (b) contacting the surface-bound complex with a first detection reagent for the analyte comprising a first proximity probe and a second detection reagent for the analyte comprising a second proximity probe to form a detection complex comprising said binding reagent, said analyte and said first and second detection reagents; (c) contacting the detection complex formed in (b) with one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe, the contacting step (c) is performed under conditions sufficient to ligate the first and second proximity probes to form a target sequence; (d) amplifying the target sequence to generate an amplicon comprising a plurality of detection sequences and an anchoring sequence complement; (e) hybridizing the anchoring sequence to the anchoring sequence complement; (f) hybridizing a plurality of detection probes to the plurality of detection probe sequences; and (g) measuring the amount of analyte bound to the surface.

Another embodiment is a method of detecting an analyte of interest in a sample comprising: (a) contacting the sample with a surface comprising (i) a binding reagent for the analyte, and (ii) an anchoring reagent comprising an anchoring sequence complementary to an amplicon sequence, wherein the contacting step forms a surface-bound complex between the analyte and the binding reagent; (b) contacting the surface-bound complex with a first detection reagent for the analyte comprising a first proximity probe and a second detection reagent for the analyte comprising a second proximity probe to form a detection complex comprising said binding reagent, said analyte and said first and second detection reagents; (c) contacting the detection complex formed in (b) with one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe, the contacting step (c) is performed under conditions sufficient to form a circular DNA template; (d) amplifying the circular DNA template to generate an amplicon comprising a plurality of detection sequences and an anchoring sequence complement; (e) hybridizing the anchoring sequence to the anchoring sequence complement; (f) hybridizing a plurality of detection probes to the plurality of detection probe sequences; and (g) measuring the amount of analyte bound to the surface.

The method also provides a method of detecting an analyte of interest in a sample comprising: (a) contacting the sample with two detection reagents for the analyte to form a detection complex, wherein the two detection reagents comprise a first proximity probe and a second proximity probe, respectively; (b) contacting the detection complex formed in (a) with a surface comprising (i) a binding reagent for the analyte and (ii) an anchoring reagent comprising an anchoring sequence complementary to an amplicon sequence, wherein the contacting step (b) forms a surface-bound complex; (c) contacting the surface-bound complex formed in (b) with one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe, the contacting step (c) is performed under conditions sufficient to ligate the first and second proximity probes to form a target sequence; (d) amplifying the target sequence to generate an amplicon comprising a plurality of detection sequences and an anchoring sequence complement; (e) hybridizing the anchoring sequence to the anchoring sequence complement; (f) hybridizing a plurality of detection probes to the plurality of detection probe sequences; and (g) measuring the amount of analyte bound to the surface.

Also provided is a method of detecting an analyte of interest in a sample comprising: a. Contacting the sample with two detection reagents for the analyte to form a detection complex, wherein the two detection reagents comprise a first proximity probe and a second proximity probe, respectively; (b) contacting the detection complex formed in (a) with a surface comprising (i) a binding reagent for the analyte and (ii) an anchoring reagent comprising an anchoring sequence complementary to an amplicon sequence, wherein the contacting step (b) forms a surface-bound complex; (c) contacting the surface-bound complex formed in (b) with one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe, the contacting step (c) is performed under conditions sufficient to form a circular DNA template; (d) amplifying the circular DNA template to generate an amplicon comprising a plurality of detection sequences and an anchoring sequence complement; (e) hybridizing the anchoring sequence to the anchoring sequence complement; (f) hybridizing a plurality of detection probes to the plurality of detection probe sequences; and (g) measuring the amount of analyte bound to the surface.

Also contemplated is a method of detecting a plurality of analytes of interest in a sample comprising: (a) contacting the sample with a surface comprising a plurality of discrete binding domains, each binding domain comprising (i) a binding reagents for an analyte, and (ii) an anchoring reagent comprising an anchoring sequence complementary to an amplicon sequence, wherein the contacting step forms a plurality of surface-bound complexes; (b) contacting each of the surface-bound complexes with two detection reagents for the analyte to form a plurality of detection complexes, wherein the two detection reagents comprise a first proximity probe and a second proximity probe, respectively; (c) contacting each detection complex formed in (b) with one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe, the contacting step (c) is performed under conditions sufficient to ligate the first and second proximity probes to form a plurality of target sequences; (d) amplifying the plurality of target sequences to generate a plurality of amplicons each comprising a detection sequence and an anchoring sequence complement; (e) hybridizing each anchoring sequence to the anchoring sequence complement; (f) hybridizing a plurality of detection probes to the plurality of detection probe sequences; and (g) measuring the amount of analytes bound to the surface.

Moreover, the invention includes a method of detecting a plurality of analytes of interest in a sample comprising: (a) contacting the sample with a surface comprising a plurality of discrete binding domains, each binding domain comprising (i) a binding reagent for an analyte, and (ii) an anchoring reagent comprising an anchoring sequence complementary to an amplicon sequence, wherein the contacting step forms a plurality of surface-bound complexes; (b) contacting each of the surface-bound complexes with two detection reagents for the analyte to form a plurality of detection complexes, wherein the two detection reagents comprise a first proximity probe and a second proximity probe, respectively; (c) contacting each detection complex formed in (b) with one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe, the contacting step (c) is performed under conditions sufficient to form a plurality of circular DNA templates; (d) amplifying the plurality of circular DNA templates to generate a plurality of amplicons each comprising a plurality of detection sequences and an anchoring sequence complement; (e) hybridizing each anchoring sequence to the anchoring sequence complement; (f) hybridizing a plurality of detection probes to the plurality of detection probe sequences; and (g) measuring the amount of analytes bound to the surface.

In addition, the invention provides a kit for the measurement of an analyte of interest in a sample, the kit comprising: (a) a surface comprising a binding reagent for the analyte and an anchoring reagent comprising an anchoring sequence complementary to an amplicon sequence; and (b) in one or more containers, compartments, or vessels: (i) two detection reagents for the analyte, wherein the two detection reagents comprise a first proximity probe and a second proximity probe, respectively; (ii) one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe; and (iii) one or more detection probes complementary to the detection probe sequence.

The invention includes a kit for the measurement of an analyte of interest in a sample, the kit comprising: (a) a surface comprising a binding reagent for the analyte and an anchoring reagent comprising an anchoring sequence complementary to an amplicon sequence; and (b) in one or more containers, compartments, or vessels: (i) two detection reagents for the analyte, wherein the two detection reagents comprise a first proximity probe and a second proximity probe, respectively; (ii) one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe; and (iii) one or more detection probes complementary to the detection probe sequence.

Another embodiment is a kit for the measurement of a plurality of analytes of interest in a sample, the kit comprising: (a) a surface comprising a plurality of discrete binding domains, each binding domain comprising (i) a binding reagent for an analyte and (ii) an anchoring reagent comprising an anchoring sequence complementary to an amplicon sequence; and (b) in one or more containers, compartments, or vessels: (i) two detection reagents for each analyte, wherein the two detection reagents comprise a first proximity probe and a second proximity probe, respectively; (ii) one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe; and (iii) one or more detection probes complementary to the detection probe sequence.

The invention also provides a method of detecting an analyte of interest in a sample comprising: (a) contacting the sample with a surface comprising a binding reagent for the analyte, wherein the contacting step forms a surface-bound complex between the analyte and the binding reagent; (b) contacting the surface-bound complex with two detection reagents for the analyte to form a detection complex, wherein the two detection reagents comprise a first proximity probe and a second proximity probe, respectively; (c) contacting the detection complex formed in (b) with one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe, the contacting step (c) is performed under conditions sufficient to ligate the first and second proximity probes to form a target sequence; (d) amplifying the target sequence to generate an amplicon comprising a plurality of detection sequences; (e) hybridizing a plurality of detection probes to the plurality of detection probe sequences; and (f) measuring the amount of analyte bound to the surface.

Still further, the invention includes a method of detecting an analyte of interest in a sample comprising: (a) contacting the sample with a surface comprising a binding reagent for the analyte, wherein the contacting step forms a surface-bound complex between the analyte and the binding reagent; (b) contacting the surface-bound complex with two detection reagents for the analyte to form a detection complex, wherein the two detection reagents comprise a first proximity probe and a second proximity probe, respectively; (c) contacting the detection complex formed in (b) with one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe, the contacting step (c) is performed under conditions sufficient to form a circular DNA template; (d) amplifying the circular DNA template to generate an amplicon comprising a plurality of detection sequences; (e) hybridizing a plurality of detection probes to the plurality of detection probe sequences; and (f) measuring the amount of analyte bound to the surface.

The invention contemplates a method of detecting an analyte of interest in a sample comprising: (a) contacting the sample with two detection reagents for the analyte to form a detection complex, wherein the two detection reagents comprise a first proximity probe and a second proximity probe, respectively; (b) contacting the detection complex formed in (a) with a surface comprising a binding reagent for the analyte, wherein the contacting step (b) forms a surface-bound complex; (c) contacting the surface-bound complex formed in (b) with one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe, the contacting step (c) is performed under conditions sufficient to ligate the first and second proximity probes to form a target sequence; (d) amplifying the target sequence to generate an amplicon comprising a plurality of detection sequences and an anchoring sequence complement; (e) hybridizing a plurality of detection probes to the plurality of detection probe sequences; and (f) measuring the amount of analyte bound to the surface.

Also provided is a method of detecting an analyte of interest in a sample comprising: (a) contacting the sample with two detection reagents for the analyte to form a detection complex, wherein the two detection reagents comprise a first proximity probe and a second proximity probe, respectively; (b) contacting the detection complex formed in (a) with a surface comprising a binding reagent for the analyte, wherein the contacting step (b) forms a surface-bound complex; (c) contacting the surface-bound complex formed in (b) with one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe, the contacting step (c) is performed under conditions sufficient to form a circular DNA template; (d) amplifying the circular DNA template to generate an amplicon comprising a plurality of detection sequences; (e) hybridizing a plurality of detection probes to the plurality of detection probe sequences; and (f) measuring the amount of analyte bound to the surface.

Further provided is a method of detecting a plurality of analytes of interest in a sample comprising: (a) contacting the sample with a surface comprising a plurality of discrete binding domains, each binding domain comprising a binding reagents for an analyte, wherein the contacting step forms a plurality of surface-bound complexes; (b) contacting each of the surface-bound complexes with two detection reagents for the analyte to form a plurality of detection complexes, wherein the two detection reagents comprise a first proximity probe and a second proximity probe, respectively; (c) contacting each detection complex formed in (b) with one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe, the contacting step (c) is performed under conditions sufficient to ligate the first and second proximity probes to form a plurality of target sequences; (d) amplifying the plurality of target sequences to generate a plurality of amplicons each comprising a detection sequence; (e) hybridizing a plurality of detection probes to the plurality of detection probe sequences; and (f) measuring the amount of analytes bound to the surface.

Another embodiment is a method of detecting a plurality of analytes of interest in a sample comprising: (a) contacting the sample with a surface comprising a plurality of discrete binding domains, each binding domain comprising a binding reagent for an analyte, wherein the contacting step forms a plurality of surface-bound complexes; (b) contacting each of the surface-bound complexes with two detection reagents for the analyte to form a plurality of detection complexes, wherein the two detection reagents comprise a first proximity probe and a second proximity probe, respectively; (c) contacting each detection complex formed in (b) with one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe, the contacting step (c) is performed under conditions sufficient to form a plurality of circular DNA templates; (d) amplifying the plurality of circular DNA templates to generate a plurality of amplicons each comprising a plurality of detection sequences; (e) hybridizing a plurality of detection probes to the plurality of detection probe sequences; and (f) measuring the amount of analytes bound to the surface.

In addition, the invention includes a kit for the measurement of an analyte of interest in a sample, the kit comprising: (a) a surface comprising a binding reagent for the analyte; and (b) in one or more containers, compartments, or vessels: (i) two detection reagents for the analyte, wherein the two detection reagents comprise a first proximity probe and a second proximity probe, respectively; (ii) one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe; and (iii) one or more detection probes complementary to the detection probe sequence.

Also provided is a kit for the measurement of an analyte of interest in a sample, the kit comprising: (a) a surface comprising a binding reagent for the analyte; and (b) in one or more containers, compartments, or vessels: (i) two detection reagents for the analyte, wherein the two detection reagents comprise a first proximity probe and a second proximity probe, respectively; (ii) one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe; and (iii) one or more detection probes complementary to the detection probe sequence.

Further provided is a kit for the measurement of a plurality of analytes of interest in a sample, the kit comprising: (a) a surface comprising a plurality of discrete binding domains, each binding domain comprising a binding reagent for an analyte; and (b) in one or more containers, compartments, or vessels: (i) two detection reagents for each analyte, wherein the two detection reagents comprise a first proximity probe and a second proximity probe, respectively; (ii) one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe; and (iii) one or more detection probes complementary to the detection probe sequence.

BRIEF DESCRIPTION OF DRAWINGS

FIG. 1(a)-(b) illustrate the formation of a sandwich immunoassay complex and the attachment of an amplified oligonucleotide product that contains multiple detection labeling sites, thereby amplifying the detectable signal for each individual binding event.

FIG. 1(b) shows the addition of an anchoring reagent including an anchoring oligonucleotide sequence that is complementary to a sequence of the amplicon that forms as the assay method progresses.

FIG. 3(a) also includes an amplification reagent that includes an anchoring oligonucleotide sequence that is complementary to a sequence of the amplicon that forms as the assay method progresses. FIG. 3(c) depicts an embodiment with Circ-1 (SEQ ID NO: 3) and Circ-2 (SEQ ID NO: 4) hybridized to PP1 (SEQ ID NO: 1) and PP2 (SEQ ID NO: 2). In this alternative embodiment, the anchoring reagent is omitted.

FIGS. 4 and 5(a)-(b) illustrate alternative methods of generating an amplicon that can be amplified by rolling circle amplification.

FIG. 6(a)-(c) illustrate an alternative embodiment in which a portion of each of the proximity probes in the sandwich complex is temporarily protected by short strands of RNA hybridized to each segment. Those strands are enzymatically removed to allow the proximity probes to hybridize to one another and the chain to be extended.

FIG. 7(a)-(c) show a further embodiment in which proximity probes are attached to the capture reagent and a detection reagent, and a portion of each proximity probe is temporarily protected by short strands of RNA hybridized thereto, as described above in reference to FIG. 6(a)-(c).

DETAILED DESCRIPTION OF THE INVENTION

Figure 2:
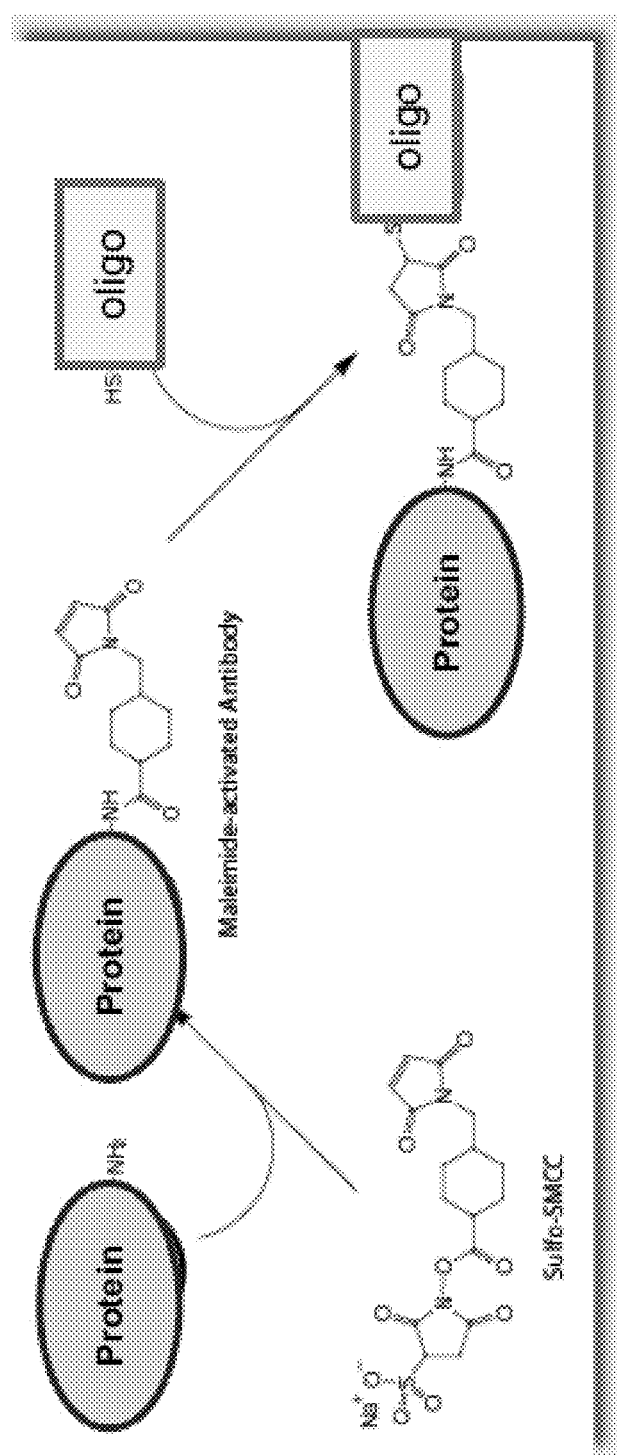
FIG. 2 shows one method of attaching an oligonucleotide to a protein.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention is designed to improve immunoassay methods by amplifying the signal from labeled antigen-antibody complexes and optionally, anchoring that complex to overcome instability that may arise from low antibody affinity and/or the attachment of a high molecular weight label or labeling site. The invention includes methods that improve on existing techniques by (i) attaching an amplified oligonucleotide product that contains multiple detection labeling sites to the sandwich immunoassay complex formed in a sandwich immunoassay, thereby amplifying the detectable signal for each individual binding event, and optionally, (ii) anchoring the sandwich immunoassay complex and the attached amplicon. In a preferred embodiment, the method includes attaching an amplified oligonucleotide product that includes multiple detection labeling sites to the sandwich immunoassay complex, and anchoring the complex to the surface to ensure that the complex is retained on the surface. This modified immunoassay method can be used to detect extremely low numbers of binding events, even individual antigen-antibody complexes. The basic approach is not limited to immunoassays and can be used to carry out binding assays using other classes of binding reagents.

One embodiment of the invention is illustrated in FIG. 1(a). The binding surface (101) includes a capture reagent (102) that binds analyte, A, and an adjacent anchoring reagent (103) that includes an anchoring oligonucleotide sequence (104). The anchoring sequence is designed to be complementary to a portion of an amplicon that is extended from the sandwich immunoassay complex as the assay method progresses. The binding surface is contacted with a sample containing the analyte, which then binds to the surface-bound capture reagent. The surface is also contacted with one or more detection reagents (105 and 106) that bind analyte A.

In a preferred embodiment, two detection reagents, a first detection reagent (105) and a second detection reagent (106) are added, which bind to the surface bound analyte to form a sandwich complex (109) in which three binding reagents: the capture reagent and two detection reagents are bound to the analyte. The first detection reagent includes a first oligonucleotide probe (referred to as the first proximity probe (107)) and the second detection reagent includes a second oligonucleotide probe (referred to as the second proximity probe (108)). The proximity probes are designed such that the first proximity probe is extended under specified amplification conditions, but only when both proximity probes are present in the sandwich complex.

In one embodiment, a proximity ligation amplification (PLA) is carried out to extend the first proximity probe. The sandwich complex comprising the two proximity probes is contacted with one or more connector oligonucleotides/probes (110). Preferably, the connector probes include a first connector probe that hybridizes to a first region on the first proximity probe and a first region on the second proximity probe; and a second connector probe that hybridizes to a second non-overlapping region of the first proximity probe and a second non-overlapping region of the second proximity probe. Ligation of hybridized connector sequences forms a circular oligonucleotide that is then used to extend the first proximity probe by rolling circle amplification (RCA) of the circle. Suitable probe designs and amplification conditions for proximity ligation amplification are well established in the art. A unique aspect of the present invention is the inclusion in one of the connector probes of the same sequence as is used in the anchoring reagent. During extension of the first proximity probe, the extended region thereby includes the complement of the anchoring sequence, which hybridizes to the anchoring reagent, thereby stabilizing the sandwich complex and preventing dissociation of the first proximity probe. The extended first proximity probe may contain detectable labels (e.g., by inclusion of labeled nucleotides during the RCA extension reaction) that can be measured to measure the amount of analyte on the surface. Alternatively, a plurality of labeled probes comprising detectable labels are added and hybridized to the extended first proximity probe, and the amount of analyte bound to the surface is measured. An alternative embodiment of the invention is illustrated in FIG. 1(b). In this embodiment, the anchoring reagent is omitted.

The skilled artisan in the field of binding assays will readily appreciate the scope of binding reagents and companion binding partners that may be used in the present methods. A non-limiting list of such pairs include (in either order) receptor/ligand pairs, antibodies/antigens, natural or synthetic receptor/ligand pairs, amines and carbonyl compounds (i.e., binding through the formation of a Schiff's base), hapten/antibody pairs, antigen/antibody pairs, epitope/antibody pairs, mimitope/antibody pairs, aptamer/target molecule pairs, hybridization partners, and intercalater/target molecule pairs. In one embodiment, the binding assays employ antibodies or other receptor proteins as binding reagents. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. *J. Cell Physiol.*, 67 (Suppl); 51-64 (1966) and Hochman, 1. Inbar, D. and Givol, D. *Biochemistry* 12: 1130 (1973)), as well as antibody constructs that have been chemically modified, e.g., by the introduction of a detectable label.

The anchoring reagent includes an anchoring sequence that is directly or indirectly bound (e.g., through binding reactions) to the surface, e.g., using methods established in the art for immobilizing oligonucleotides. In one embodiment, the anchoring reagent comprises a protein linked or otherwise bound to the anchoring sequence. In this embodiment, any protein can be used that can be immobilized on a surface and modified by an anchoring oligonucleotide. Non-limiting examples include streptavidin, avidin, or bovine serum albumin (BSA). In a preferred embodiment, the anchoring reagent comprises BSA. The protein can be modified by an anchoring oligonucleotide and attached to a surface using known methods, e.g., as illustrated in FIG. 2, using sulfosuccinimidyl-4-(N-maleimidomethyl)cyclo-hexane-1-carboxylate (Sulfo-SMCC), a well-established heterobifunctional cross-linking agent. Reaction of the N-hydroxysuccinimide (NHS) group of SMCC with bovine serum albumin (BSA) labels the BSA with thiol-reactive maleimide groups. The maleimide groups are, in turn, reacted with thiol-modified oligonucleotides to form BSA-oligonucleotide conjugates that are linked through stable thioether bonds. In one specific example, arrays are formed by printing arrays of the BSA-oligonucleotide conjugates on graphitic carbon surfaces, preferably screen printed carbon ink electrodes. Alternatively, if the protein is avidin or streptavidin, the anchoring sequence can be linked to biotin and joined to immobilized avidin or streptavidin through biotin-avidin or biotin-streptavidin interactions.

The anchoring oligonucleotide attached to the anchoring reagent can be any sequence that will hybridize to the amplicon that develops during the amplification process. In a preferred embodiment, the anchoring oligonucleotide sequence comprises a poly(A) sequence attached to the anchor sequence complementary to an inert region of the amplicon sequence or a portion thereof. In one embodiment, a sequence that is complementary to the full length of the inert region of the amplicon is included, about 25 nucleotides in length), alone or in combination with a poly(A) arm of e.g., up to 30 nucleotides in length. Preferably, the anchoring oligonucleotide is selected from: (i) (full length complement to the inert region of the amplicon, 25 nucleotides in length)-(20 nucleotide poly (A) arm); or (ii)

(complement to a portion of the inert region of the amplicon, 15 nucleotides in length)-(30 nucleotide poly (A) arm).

Any suitable amplification technique can be used to generate the amplicon, including but not limited to, PCR (Polymerase Chain Reaction), LCR (Ligase Chain Reaction), SDA (Strand Displacement Amplification), 3SR (Self-Sustained Synthetic Reaction), and isothermal amplification methods, e.g., helicase-dependent amplification and rolling circle amplification (RCA). In a preferred embodiment, RCA is used because it has significant advantages in terms of sensitivity, multiplexing, dynamic range and scalability. Techniques for RCA are known in the art (see, e.g., Baner et al, Nucleic Acids Research, 26:5073 5078, 1998; Lizardi et al., Nature Genetics 19:226, 1998; Schweitzer et al. Proc. Natl. Acad. Sci. USA 97:10113 119, 2000; Faruqi et al., BMC Genomics 2:4, 2000; Nallur et al., Nucl. Acids Res. 29:e118, 2001; Dean et al. Genome Res. 11:1095 1099, 2001; Schweitzer et al., Nature Biotech. 20:359 365, 2002; U.S. Pat. Nos. 6,054,274, 6,291,187, 6,323,009, 6,344,329 and 6,368,801). Several different variants of RCA are known, including linear RCA (LRCA) and exponential RCA (ERCA). RCA generates many thousands of copies of a circular template, with the chain of copies attached to the original target DNA, allowing for spatial resolution of target and rapid amplification of the signal. RCA facilitates (i) detection of single target molecules; (ii) amplification of signals from proteins as well as DNA and RNA; (iii) identifying the location of molecules that have been amplified on a solid surface; (iv) measurement of many different targets simultaneously; and (v) analysis of one or more targets in solution or solid phase.

Figure 3A:
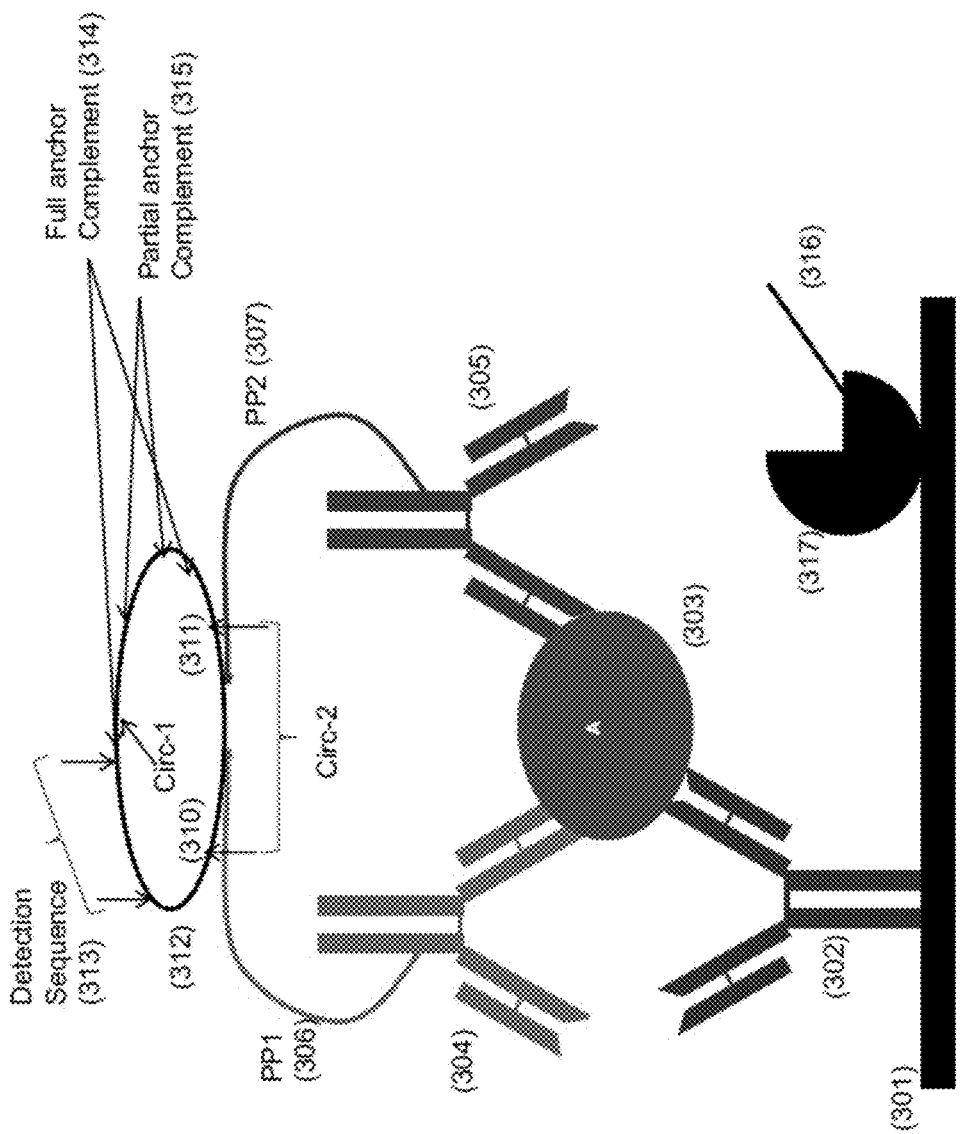
FIG. 3(a) illustrates a preferred embodiment of the invention in which a surface bound complex is formed between a capture reagent, the analyte, and two detection reagents, each attached to a first and second proximity probe, respectively. Two connector probes are litigated to form a circular DNA template that is amplified by rolling circle amplification. Circ-1, SEQ ID NO: 4; Circ-2, SEQ ID NO: 5; PP1, SEQ ID NO: 1 (poly-A tail truncated); PP2, SEQ ID NO: 2.
Figure 3B:
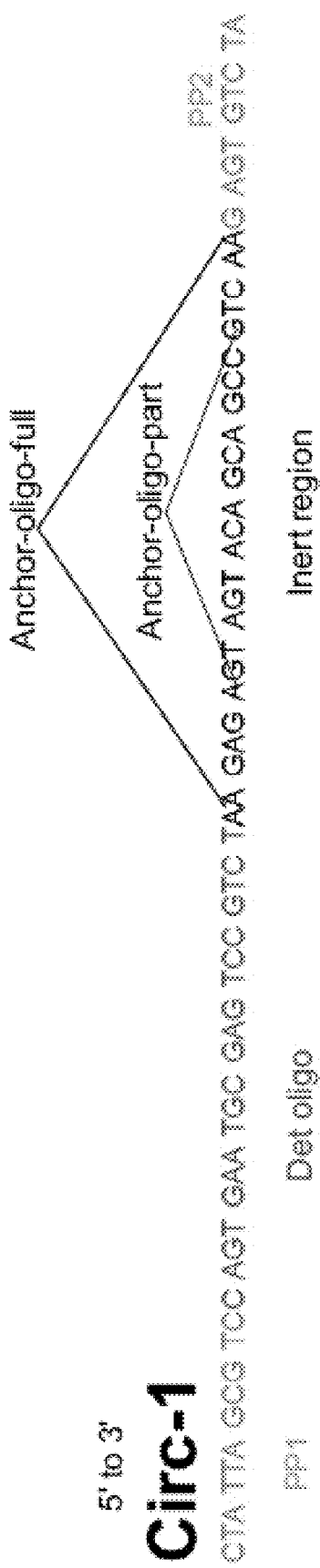
FIG. 3(b) shows an exemplary sequence (SEQ ID NO: 3) of the first circular DNA template Circ-1, a detection oligonucleotide sequence, the inert region of the amplicon, and a portion PP2, which is designed to hybridize to the second proximity probe.

A specific embodiment of the invention is depicted in FIG. 3(a). A complex is formed on a surface (301) between a capture reagent (302), the analyte (303) and two detection reagents (304 and 305), each including a first proximity probe (306) (PP1, SEQ ID NO: 1) and a second proximity probe (307) (PP2, SEQ ID NO: 2), respectively. First and second connector oligonucleotides Circ-1 (308) (SEQ ID NO: 3) and Circ-2 (309) (SEQ ID NO: 4), respectively, in FIG. 3(a)) are added, which when both proximity probes are present in the complex, each hybridize to and bridge the two proximity probes. The bound connector probes are ligated at ligations sites 1 and 2 (310 and 311), respectively to form a circular DNA template (312). The circular DNA template is amplified by rolling circle amplification to extend the first proximity probe and, thereby, generate an amplicon comprising a plurality of detection sequences (313) and an anchoring oligonucleotide sequence complement (314) (including a partial anchoring sequence complement (315)). The anchoring oligonucleotide sequence (316) (attached to a capture moiety (317)) and its complement hybridize, a plurality of detection probes are hybridized to the plurality of detection probe sequences, and the amount of analyte bound to the surface is measured (not shown but illustrated in FIG. 1(a)). FIG. 3(b) shows an exemplary sequence of the first circular DNA template Circ-1 (308) (SEQ ID NO: 3), which is designed to hybridize to the first proximity probe (PP1), a detection oligonucleotide sequence, the inert region of the amplicon (which can be used in whole or in part to bind to the anchoring oligonucleotide sequence), and a portion PP2 (which is designed to hybridize to the second proximity probe). An alternative embodiment is depicted in FIG. 3(c). A complex is formed on a surface (318) between a binding reagent (319), the analyte (320) and two detection reagents (321 and 322), each including a first and second proximity probe (323 and 324), respectively. First and second circularization oligonucleotides (Circ-1 (325) (SEQ ID NO: 3) and Circ-2 (326) (SEQ ID NO: 4), respectively in FIG. 3(c)) are added, which ligate to each other at ligations sites 1 and 2 (327 and 328), respectively, to form a circular DNA template (329). The circular DNA template is amplified by rolling circle amplification to generate an amplicon comprising a plurality of detection sequences (330). A plurality of detection probes are hybridized to the plurality of detection probe sequences, and the amount of analyte bound to the surface is measured. It is to be understood that the poly-A tails of proximity probes PP1 and PP2 as disclosed in the Figures, such as FIG. 3(c), may vary in the number of adenine repeats specifically shown in the Figures, relative to the disclosed PP1 and/or PP2 sequences, without intending to alter the sequences disclosed herein.

Figure 4:
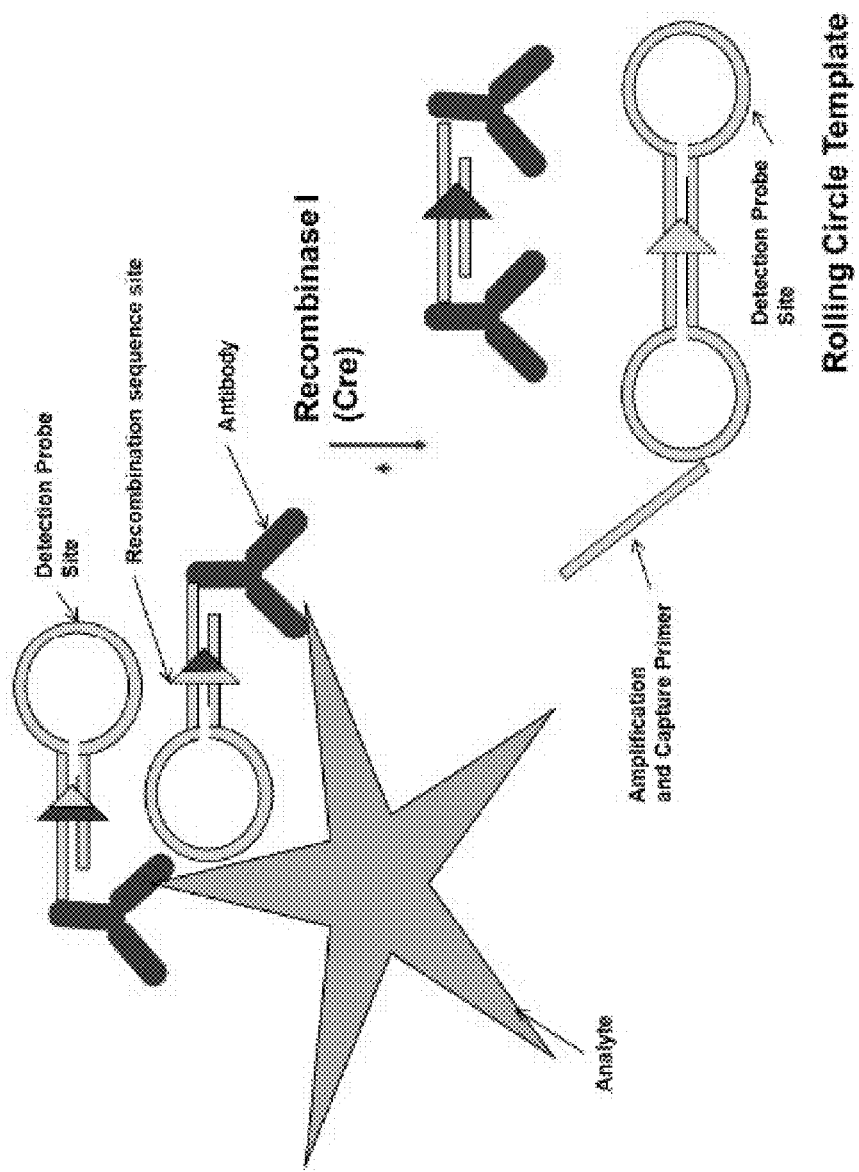

Another approach to generating a target sequence that is amplified by RCA or any suitable amplification method is illustrated in FIG. 4. In this embodiment, each of the proximity probes can fold into a looped hairpin structure. The formation of these hairpin structures generates a single stranded loop and double stranded portion containing a recombination signal. Recombinase is added drive the recombination of the two hairpin structures to form a circular DNA template, which is subsequently subjected to RCA as described above. The amplicon is labeled and optionally anchored to an anchoring reagent and analyte is detected. The key element of this embodiment is the ability of recombinases to catalyze the site specific recombination of DNA containing sequence specific recombination sites. For example, Cre Recombinase from the bacteriophage P1 catalyzes recombination at sites containing loxP sites and other non-limiting examples include but are not limited to Flippase (flp, from Yeast), Hin (Salmonella), and Tre, an engineered (evolved) version of Cre. This alternative approach does not require the addition of additional components such as oligonucleotide templates, ATP and dNTPs. In this embodiment, the loxP (recombination) sites are preferably modified to be non-symmetrical, resulting in a shift in the normal equilibrium towards the formation of the desired recombined product. This is illustrated in FIG. 4, with the light/dark shading of the recombination sites.

Moreover, FIG. 5(a) illustrates yet another method to generate a target sequence that is amplified by RCA or any suitable amplification method. Each of the proximity probes attached to the detection reagents include a loxP site that enables site specific recombination between the two oligonucleotides by Cre recombinase, resulting in the formation of a new oligonucleotide sequence that is composed of the 5' portion of one proximity probe and the 3' portion of the other proximity probe, that flank the lox P sites. The newly created target sequence can be subsequently amplified by any suitable method, labeled, optionally anchored, and detected as described above. FIG. 5(a) illustrates this embodiment using the T7 RNA polymerase promoter as the operable element for amplification. It will also be understood that other RNA polymerase sites such as T3 and SP6 linked at either the 3 or 5' portions of the proximity probes, are equally suitable for use in this method. In this embodiment, the loxP (recombination) sites are preferably modified to be non-symmetrical, resulting in a shift in the normal equilibrium towards the formation of the desired recombined product. As shown in FIG. 5(b), the method can also be used to generate a circular DNA template that can be used in RCA.

The various reagents employed in the method can be combined in one or more additional or alternative steps without departing from the spirit or scope of the invention. For example, the reagents can be combined sequentially, e.g., analyte is added to the binding reaction on the surface, followed by the addition of detection reagent(s), and then amplification, and detection, such that the method is carried out on the surface. Alternatively, one or more reagents can be combined in solution and then contacted with the surface. For example, the analyte can be combined with the detection reagents and then contacted with the surface, followed by amplification and detection, and/or the detection reagents can be combined with the analyte, the PLA amplification carried out in solution, and the resulting complex contacted by the surface to carry out the remaining steps of the methods.

Examples of samples that may be analyzed by the methods of the present invention include, but are not limited to food samples (including food extracts, food homogenates, beverages, etc.), environmental samples (e.g., soil samples, environmental sludges, collected environmental aerosols, environmental wipes, water filtrates, etc.), industrial samples (e.g., starting materials, products or intermediates from an industrial production process), human clinical samples, veterinary samples and other samples of biological origin. Biological samples that may be analyzed include, but are not limited to, feces, mucosal swabs, physiological samples and/or samples containing suspensions of cells. Specific examples of biological samples include blood, serum, plasma, feces, mucosal swabs, tissue aspirates, tissue homogenates, cell cultures and cell culture supernatants (including cultures of eukaryotic and prokaryotic cells), urine, saliva, sputum, and cerebrospinal sample.

Analytes that may be measured using the methods of the invention include, but are not limited to proteins, toxins, nucleic acids, microorganisms, viruses, cells, fungi, spores, carbohydrates, lipids, glycoproteins, lipoproteins, polysaccharides, drugs, hormones, steroids, nutrients, metabolites and any modified derivative of the above molecules, or any complex comprising one or more of the above molecules or combinations thereof. The level of an analyte of interest in a sample may be indicative of a disease or disease condition or it may simply indicate whether the patient was exposed to that analyte.

The assays of the present invention may be used to determine the concentration of one or more, e.g., two or more analytes in a sample. Thus, two or more analytes may be measured in the same sample. Panels of analytes that can be measured in the same sample include, for example, panels of assays for analytes or activities associated with a disease state or physiological conditions. Certain such panels include panels of cytokines and/or their receptors (e.g., one or more of TNF-alpha, TNF-beta, IL1-alpha, IL1-beta, IL2, IL4, IL6, IL-10, IL-12, IFN-y, etc.), growth factors and/or their receptors (e.g., one or more of EGF, VGF, TGF, VEGF, etc.), drugs of abuse, therapeutic drugs, vitamins, pathogen specific antibodies, auto-antibodies (e.g., one or more antibodies directed against the Sm, RNP, SS-A, SS-alpha, J0-1, and Scl-70 antigens), allergen-specific antibodies, tumor markers (e.g., one or more of CEA, PSA, CA-125 II, CA 15-3, CA 19-9, CA 72-4, CYFRA 21-1, NSE, AFP, etc.), markers of cardiac disease including congestive heart disease and/or acute myocardial infarction (e.g., one or more of Troponin T, Troponin I, myoglobin, CKMB, myeloperoxidase, glutathione peroxidase, β-natriuretic protein (BNP), alpha-natriuretic protein (ANP), endothelin, aldosterone, C-reactive protein (CRP), etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (alpha-amyloid, beta-amyloid, Aβ 42, Aβ 40, Aβ 38, Aβ 39, Aβ 37, Aβ 34, tau-protein, etc.), markers of osteoporosis (e.g., one or more of cross-linked Nor C-telopeptides, total deoxypyridinoline, free deoxypyridinoline, osteocalcin, alkaline phosphatase, C-terminal propeptide of type I collagen, bone-specific alkaline phosphatase, etc.), markers of fertility state or fertility associated disorders (e.g., one or more of Estradiol, progesterone, follicle stimulating hormone (FSH), lutenizing hormone (LH), prolactin, hCG, testosterone, etc.), markers of thyroid disorders (e.g., one or more of thyroid stimulating hormone (TSH), Total T3, Free T3, Total T4, Free T4, and reverse T3), and markers of prostate cancer (e.g., one or more of total PSA, free PSA, complexed PSA, prostatic acid phosphatase, creatine kinase, etc.). Certain embodiments of invention include measuring, e.g., one or more, two or more, four or more or 10 or more analytes associated with a specific disease state or physiological condition (e.g., analytes grouped together in a panel, such as those listed above; e.g., a panel useful for the diagnosis of thyroid disorders may include e.g., one or more of thyroid stimulating hormone (TSH), Total T3, Free T3, Total T4, Free T4, and reverse T3).

The methods of the present invention are designed to allow detection of a wide variety of biological and biochemical agents, as described above. In one embodiment, the methods may be used to detect pathogenic and/or potentially pathogenic virus, bacteria and toxins including biological warfare agents ("BWAs") in a variety of relevant clinical and environmental matrices, including and without limitation, blood, sputum, stool, filters, swabs, etc. A non-limiting list of pathogens and toxins that may be analyzed (alone or in combination) using the methods of the present invention is *Bacillus anthracis* (anthrax), *Yersinia pestis* (plague), *Vibrio cholerae* (cholera), *Francisella tularensis* (tularemia), *Brucella* spp. (Brucellosis), *Coxiella burnetii* (Q fever), orthopox viruses including variola virus (smallpox), viral encephalitis, Venezuelan equine encephalitis virus (VEE), western equine encephalitis virus (WEE), eastern equine encephalitis virus (EEE), Alphavirus, viral hemorrhagic fevers, Arenaviridae, Bunyaviridae, Filoviridae, Flaviviridae, Ebola virus, staphylococcal enterotoxins, ricin, botulinum toxins, *Clostridium botulinum*, mycotoxin, *Fusarium, Myrotecium, Cephalosporium, Trichoderma, Verticimonosporium, Stachybotrys*, glanders, wheat fungus, *Bacillus globigii, Serratia marcescens*, yellow rain, trichothecene mycotoxins, *Salmonella typhimurium*, aflatoxin, *Xenopsylla cheopis, Diamanus montamus*, alastrim, monkeypox, Arenavirus, Hantavirus, Lassa fever, Argentine hemorrhagic fevers, Bolivian hemorrhagic fevers, Rift Valley fever virus, Crimean-Congo virus, Hanta virus, Marburg hemorrhagic fevers, yellow fever virus, dengue fever viruses, influenza (including human and animal strains including H5N1 avian influenza), human immunodeficiency viruses I and II (HIV I and II), hepatitis A, hepatitis B, hepatitis C, hepatitis (non-A, B or C), Enterovirus, Epstein-Barr virus, Cytomegalovirus, herpes simplex viruses, *Chlamydia trachomatis, Neisseria gonorrheae, Trichomonas vaginalis*, human papilloma virus, *Treponema pallidum, Streptococcus pneumonia, Haemophilus influenzae, Mycoplasma pneumoniae, Chlamydophila pneumoniae, Legionella pneumophila, Staphylococcus aureus. Moraxella catarrhalis, Streptococcus pyogenes, Clostridium difficile, Neisseria meningitidis, Klebsiella pneumoniae, Mycobacterium tuberculosis*, coronavirus, Coxsackie A virus, rhinovirus, parainfluenza virus, respiratory syncytial virus (RSV), metapneumovirus, and adenovirus.

A wide variety of solid phases are suitable for use in the methods of the present invention including conventional solid phases from the art of binding assays. Solid phases may be made from a variety of different materials including polymers (e.g., polystyrene and polypropylene), ceramics, glass, composite materials (e.g., carbon-polymer composites such as carbon-based inks). Suitable solid phases include the surfaces of macroscopic objects such as an interior surface of an assay container (e.g., test tubes, cuvettes, flow cells, cartridges, wells in a multi-well plate, etc.), slides, assay chips (such as those used in gene or protein chip measurements), pins or probes, beads, filtration media, lateral flow media (for example, filtration membranes used in lateral flow test strips), etc.

Suitable solid phases also include particles (including but not limited to colloids or beads) commonly used in other types of particle-based assays e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like. A particle used in the present method may be comprised of any material suitable for attachment to one or more binding reagents, and that may be collected via, e.g., centrifugation, gravity, filtration or magnetic collection. A wide variety of different types of particles that may be attached to binding reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles. The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

The methods of the present invention may be used in a variety of assay devices and/or formats. The assay devices may include, e.g., assay modules, such as assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or pre-loaded in the wells, chambers, or assay regions of the assay module. These devices may employ a variety of assay formats for specific binding assays, e.g., immunoassay or immunochromatographic assays. Illustrative assay devices and formats are described herein below. In certain embodiments, the methods of the present invention may employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

The methods of the invention can be used with a variety of methods for measuring the amount of an analyte and, in particular, measuring the amount of an analyte bound to a solid phase. Techniques that may be used include, but are not limited to, techniques known in the art such as cell culture-based assays, binding assays (including agglutination tests, immunoassays, nucleic acid hybridization assays, etc.), enzymatic assays, colorometric assays, etc. Other suitable techniques will be readily apparent to one of average skill in the art. Some measurement techniques allow for measurements to be made by visual inspection, others may require or benefit from the use of an instrument to conduct the measurement.

Methods for measuring the amount of an analyte include label-free techniques, which include but are not limited to i) techniques that measure changes in mass or refractive index at a surface after binding of an analyte to a surface (e.g., surface acoustic wave techniques, surface plasmon resonance sensors, ellipsometric techniques, etc.), ii) mass spectrometric techniques (including techniques like MALDI, SELDI, etc. that can measure analytes on a surface), iii) chromatographic or electrophoretic techniques, iv) fluorescence techniques (which may be based on the inherent fluorescence of an analyte), etc.

Methods for measuring the amount of an analyte also include techniques that measure analytes through the detection of labels which may be attached directly or indirectly (e.g., through the use of labeled binding partners of an analyte) to an analyte. Suitable labels include labels that can be directly visualized (e.g., particles that may be seen visually and labels that generate an measurable signal such as light scattering, optical absorbance, fluorescence, chemiluminescence, electrochemiluminescence, radioactivity, magnetic fields, etc). Labels that may be used also include enzymes or other chemically reactive species that have a chemical activity that leads to a measurable signal such as light scattering, absorbance, fluorescence, etc. The use of enzymes as labels has been well established in in Enzyme-Linked ImmunoSorbent Assays, also called ELISAs, Enzyme ImmunoAssays or EIAs. In the ELISA format, an unknown amount of antigen is affixed to a surface and then a specific antibody is washed over the surface so that it can bind to the antigen. This antibody is linked to an enzyme, and in the final step a substance is added that the enzyme converts to a product that provides a change in a detectable signal. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the invention may benefit from or require a wash step to remove unbound components (e.g., labels) from the solid phase Accordingly, the methods of the invention may comprise such a wash step.

In one embodiment, an analyte(s) of interest in the sample may be measured using electrochemiluminescence-based assay formats, e.g. electrochemiluminescence (ECL) based immunoassays. The high sensitivity, broad dynamic range and selectivity of ECL are important factors for medical diagnostics. Commercially available ECL instruments have demonstrated exceptional performance and they have become widely used for reasons including their excellent sensitivity, dynamic range, precision, and tolerance of complex sample matrices. Species that can be induced to emit ECL (ECL-active species) have been used as ECL labels, e.g., i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147, 806; 5,324,457; 5,591,581; 5,597,910; 5,641,623; 5,643, 713; 5,679,519; 5,705,402; 5,846,485; 5,866,434; 5,786, 141; 5,731,147; 6,066,448; 6,136,268; 5,776,672; 5,308, 754; 5,240,863; 6,207,369; 6,214,552 and 5,589,136 and Published PCT Nos. WO99/63347; WOOO/03233; WO99/ 58962; WO99/32662; WO99/14599; WO98/12539; WO97/ 36931 and WO98/57154, all of which are incorporated herein by reference.

The methods of the invention may be applied to single-plex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) or v) that are based on temporal properties of assay signal (e.g., time, frequency or phase of a signal).

According to one embodiment of the present invention, the methods of the invention can be used to detect the presence of an analyte and/or determine the concentration of analyte molecules in a sample. In some cases, there is a correlation between the percentage of binding surfaces (e.g., binding domains) containing one or more analyte molecules and the concentration of the analyte molecules in the sample. Thus, the quantification method of certain embodiments of the invention allows for calculation of the number of analyte molecules in a sample based on the percentage of binding surfaces that contain an analyte molecule. In some embodiments, the measure of the concentration of analyte molecules in a sample will be determined using a calibration curve. Methods to determine the concentration of analyte molecules in a sample are discussed below.

Certain embodiments of present invention are distinguished by the ability to detect and/or quantify low numbers/ concentrations of analyte molecules in a sample. It is currently believed that this ability may be achieved by spatially isolating individual or small numbers of analyte molecules, for example, as when they are partitioned across an array of binding surfaces, and then detecting their presence in the binding surfaces. The presence of an analyte molecule in a binding surface can be counted in a binary fashion (e.g., zero when an analyte molecule is absent; one when an analyte molecule is present), for example by determining the presence of a detectable label in a binding surface that contains at least one analyte molecule.

In some embodiments, the plurality of analyte molecules may be partitioned such that at least some of the binding surfaces contain no analyte molecules and at least some binding surfaces contain at least one or, in certain cases, only one analyte molecule. For example, in some cases, the plurality of analyte molecules may be partitioned such that a statistically significant fraction of the binding surfaces contain no analyte molecules and a statistically significant fraction of binding surfaces contain at least one analyte molecule. In other cases, the plurality of analyte molecules may be partitioned such that a statistically significant fraction of the binding surfaces contain no analyte molecules and a statistically significant fraction of binding surfaces contain only one analyte molecule. In either case, the number of the plurality of binding surfaces and/or fraction of the plurality of binding surfaces that contain or do not contain an analyte molecule may be determined. The number and/or fraction of the plurality of binding surfaces that contain an analyte molecule can be related to the concentration of analyte molecules in the sample. In some embodiments, a measure of the concentration of analyte molecules in the sample is determined based on the determination of the number and/or fraction of the plurality of binding surfaces that contain an analyte molecule. In certain such embodiments, the measure of the concentration of the analyte molecules in the sample is determined at least in part comparison of a measured parameter to a calibration standard and/or by a Poisson and/or Gaussian distribution analysis of the number or fraction of the plurality of binding surfaces that contain an analyte molecule, as discussed more below. A "statistically significant fraction" of the binding surfaces that contain a specified quantity of dissociated species is defined as the minimum number of binding surfaces that can be reproducibly determined to contain an analyte molecule with a particular system of detection (i.e., substantially similar results are obtained for multiple essentially identical samples comprising the target analyte molecule) and that is above the background noise (e.g., non-specific binding) that is determined when carrying out the assay with a sample that does not contain any analyte molecules, divided by the total number of binding surfaces. The statistically significant fraction may be experimentally determined for a certain assay type and equipment set up (e.g., for each analyte molecule determined, each binding ligand, etc). In certain embodiments, the percentage of binding surfaces (e.g., the statistically significant fraction) which comprises only one or at least one analyte molecule is less than about 10%, less than about 5%, less than about 1%, less than about 0.5%, or less than about 0.1% of the total binding surfaces. In some cases, the percentage of binding surfaces which do not contain an analyte molecule is at least about 20%, at least about 40%, at least about 50%, at least about 60%, at least about 70%, at least about 75%, at least about 80%, at least about 90%, or at least about 95%, at least about 99%, at least about 99.5%, at least about 99.9%, or greater, of the total number of binding surfaces.

In some embodiments, a measure of the concentration of analyte molecules in the sample may be determined at least in part by comparison of a measured parameter to a calibration standard. For example, the fraction of binding surfaces that comprise an analyte molecule may be compared against a calibration curve to determine a measure of the concentration of the analyte molecule in the sample. The calibration curve may be produced by completing the assay with a plurality of standardized samples of known concentration under the conditions used to analyze the test samples. A reading may be taken for the signal related to the detection/quantification of the analyte molecules for each standardized sample, therefore allowing for the formation of a calibration curve relating the detection of the analyte molecules with a known concentration of the analyte molecule. The assay may then be completed on a sample comprising the analyte molecule in an unknown concentration, and the detection of the analyte molecules from this assay may be plotted on the calibration curve, therefore determining a measure of the concentration of the analyte molecule in the sample.

In some embodiments, the concentration of analyte molecules in the sample that may be substantially accurately determined is less than about 100 fM, less than about 10 fM, less than about 3 fM, less than about 1 fM, less than about 0.3 fM, less than about 0.1 fM, less than about 0.03 fM, or less. In some embodiments, the concentration of analyte molecules in the sample that may be substantially accurately determined is between about 5000 fM and about 0.1 fM, between about 3000 fM and about 0.1 fM, between about 1000 fM and about 0.1 fM, between about 1000 fM and about 1 fM, between about 100 fM and about 1 fM, between about 100 fM and about 0.1 fM. The concentration of analyte molecules in a sample may be considered to be substantially accurately determined if the measured concentration of the analyte molecules in the sample is within about 20% of the actual concentration of the analyte molecules in the sample. In certain embodiments, the measured concentration of the analyte molecules in the sample may be within about 10%, within about 3%, or within about 1% of the actual concentration of the analyte molecules in the sample. The accuracy of the assay method may be determined, in some embodiments, by determining the concentration of analyte molecules in a sample of a known concentration using the selected assay method.

One advantageous aspect of the methods of the invention, especially when coupled to a sensitive optical detection technique is that the signal amplification allows for the detection of individual binding event as bright points of light. Quantitation of signal, can then be carried out by counting the individual events (which can provide better sensitivity for low analyte concentrations by providing improved discrimination of binding events from background noise) or by integrating over the signal for all binding events (which can provide better dynamic range for measuring high analyte concentrations).

In the specific case of using an imaging technique to measure an optical signal (such as fluorescence, chemiluminescence or electrochemiluminescence) a binding event can be detected as a bright point source of light. When the surface density of point sources is low (e.g., when the probability of finding a point source in an R×R area—where R is the spatial resolution of the detection system—is less than 10%), it is likely that any observed point source is due to a single binding event. Under these conditions, counting events is likely to provide the most sensitive measurement. As the surface density increases, it becomes increasingly likely that it will not be possible to resolve and count individual binding events. Under these conditions, integrating the optical signal over the binding surface is likely to provide a more accurate measurement.

In one embodiment, the invention provides a kit comprising (a) surface including a binding reagent for the analyte and an anchoring reagent comprising an anchoring oligonucleotide complementary to an amplicon sequence; and (b) in one or more containers, compartments, or vessels: (ii) two detection reagents for the analyte, wherein the two detection reagents comprise a first proximity probe and a second proximity probe, respectively; (ii) one or more connector oligonucleotides including a first connector probe complementary to a first region of the first proximity probe and a first region on the second proximity probe, and a second connector probe complementary to a second non-overlapping region of the first proximity probe and a second non-overlapping region of the second proximity probe; and (iii) one or more detection probes complementary to the detection probe sequence.

In an additional embodiment, the invention provides a kit comprising (a) surface including a binding reagent for the analyte and a anchoring moiety comprising an anchoring oligonucleotide complementary to an amplicon sequence; and (b) in one or more containers, compartments, or vessels: (ii) two detection reagents for the analyte, wherein the two detection reagents comprise a first proximity probe and a second proximity probe, respectively; (ii) one or more connector oligonucleotides including a first circularization probe complementary to a first region of the first proximity probe and a first region on the second proximity probe, and a second circularization probe complementary to a second non-overlapping region of the first proximity probe and a second non-overlapping region of the second proximity probe, the contacting step (c) is performed under conditions sufficient to form a circular DNA template; and (iii) one or more detection probes complementary to the detection probe sequence.

The kit can further include one or more of the following: one or more additional reagents, buffers, polymerase, ligase, and/or dNTPs. In addition, if the one or more detection probes comprise a detectable ECL label, the kit can also include an ECL co-reactant.

Additional Alternative Embodiments

A further embodiment is illustrated in FIG. 6(a)-(c). A portion of each of the proximity probes in the sandwich immunoassay complex in panel (a) are temporarily protected by short strands of RNA hybridized to each segment. The RNA strands are enzymatically removed so that each of the proximity probes can hybridize to one another and the chain is extended by polymerase extension using biotinylated dNTPs (panel (b)). Each biotinylated base incorporated into the chain is bound to streptavidin labeled with a detectable label (panel (c)).

Yet another approach is illustrated in FIG. 7(a)-(c). Proximity probes can be attached to the anchoring reagent and a detection reagent (as shown in panel (a)) or each of the proximity probes can be attached to two detection reagents as described hereinabove (not shown). Much like the method illustrated in FIG. 6(a)-(c), a portion of each of the proximity probes are temporarily protected by short strands of RNA hybridized to each segment. The RNA strands are enzymatically removed so that each of the proximity probes can hybridize to one another and the chain is extended by polymerase extension using biotinylated dNTPs (panel (b)). Each biotinylated base incorporated into the chain is bound to streptavidin labeled with a detectable label (panel (c)).

EXAMPLES

General Protocol for Proximity Ligation and Rolling Circle Amplification

A pair of detection antibodies to a target analyte was modified by the addition of proximity probes 1 and 2 as follows: to 20 ug first detection antibody in 10 uL buffer, 1 uL 4 mM sulfo-SMCC was added, diluted in DMSO, and incubated at room temperature for 2 hours. The final concentration of the detection antibody was 2 mg/mL or higher. Three (3) uL of 100 uM thiol-modified oligonucleotide (proximity probe 1 and 2) was reduced with 4 uL of 100 mM DTT in 50 uL of 55 mM phosphate buffer, 150 mM NaCl, 20 mM EDTA, pH 7.0, for 1 hour at 37 C. The sequences of proximity probes 1 and 2 are:

```
Thiol-modified proximity probe 1:
(SEQ ID No. 1; wherein the three U resides are 2'
O-methyl RNA)
SH-AAA AAA AAA AGA CGC TAA TAG TTA AGA CGC TTU UU Thiol-modified proximity probe 2:
                                        (SEQ ID No. 2)
SH-AAA AAA AAA ATA TGA CAG AAC TAG ACA CTC TT.
```

Excess sulfo-SMCC and DTT were removed, e.g., by using three spin column separates and antibody and DNA were pooled for covalent conjugation. The solution was dialyzed against 1×PBS at 4 C overnight. Antibody-proximity probe conjugates were purified, e.g, by gel filtration to remove unconjugated antibodies and oligonucleotides.

An MSD MULTI-SPOT® plate was blocked for 1 hour with appropriate MSD® blocking solution and washed. Each binding domain on the plate included a anchoring antibody and anchoring moiety, BSA, to which an oligonucleotide specific for an amplicon is covalently attached. Twenty-five (25) μl assay diluent, calibrator, or sample (diluted as appropriate) was added to each well. The plate was incubated with shaking for 1-3 hours and each well was washed. A solution of detection antibodies labeled with proximity probes 1 and 2, prepared as described above, was added to each well, and incubated with shaking for 1-2 hours (alternatively, each individual detection antibody can be sequentially added, with each addition followed by a 1 hour incubation). A ligation mix was added to each well including the following components: (i) circularization oligonucleotide 1 (125 nM), circularization oligonucleotide 2 (125 nM), ligation buffer, ATP (1 mM), BSA (250 ug/mL), Tween 20 (0.05%), NaCl (250 mM), T4 DNA ligase (0.05 U/uL), wherein the each of the circularization oligonucleotides are:

```
Circularization oligonucleotide 1:
                                        (SEQ ID No. 3)
Phosphate-CTA TTA GCG TCC AGT GAA TGC GAG TCC GTC
TAA GAG AGT AGT AGA GCA GCC GTC AAG AGT GTC TA.

Circularization oligonucleotide 2:
                                        (SEQ ID No. 4)
Phosphate-GTT CTG TCA TAT TTA AGC GTC TTA A.
```

The plate was incubated with the ligation mix for 30 minutes at 37 C, washed to remove excess circularization oligonucleotides, and incubated with RCA mixture for 1.5 hour at 37 C, wherein the RCA mixture contains BSA (250 ug/mL), RCA buffer, dNTP (250 uM of each), Tween 20 (0.05%) Phi29 DNA polymerase (0.125 U/ml). The plate was washed and a mixture of detection probes were added and incubated for 30 minutes at 37 C, wherein the detection probe mixture includes: BSA (250 ug/ml), sonicated salmon sperm DNA (2.5 ug/ml), 2×SSC, Tween 20 (0.05%), detection probes (6.25 nM). The detection probe is STAG-(SA+Biotin)-CAG TGA ATG CGA GTC CGT CT (SEQ ID No. 5). The plate was washed with 150 μl MSD read buffer and read immediately on MSD SECTOR® 6000 Reader (plates and reader supplied by Meso Scale Discovery, Rockville, Md.).

This general procedure was used to detect the following analytes: troponinin I, Akt (total), phospho-Akt (473), phospho-Akt (308), Flu NPA, IL-12p40, IL-12p70, Abeta1-42, bridging and isotyping Ig assays using TNFalpha model system, bridging and isotyping Ig assays using Hep B surface antigen, and bridging and isotyping Ig assays using Lyme C6. In general, the increase in ECL signal relative to a standard sandwich immunoassay ranges from 0.2-100 times, average increase in background signal was from 0-10×, and the average improvement in LOD (limits of detection) was 2-30×. For certain assays tested, e.g., Troponin-1, Akt (total), IL-12p40, IL-12p70, and Abeta1-42, the presence of anchoring moiety improved signal and/or dilution linearity.

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

REFERENCES

1. U.S. Pat. No. 7,306,904
2. U.S. Pat. No. 7,320,860
3. U.S. Pat. No. 7,351,528
4. U.S. Pat. No. 7,192,703
5. U.S. Pat. No. 6,878,515
6. Zhou et al., Genome Biology (2004), 5: R28
7. Dean et al., Genome Research (2001), 11: 1095-1099
8. Soderberg et al., Methods (2008), 45: 227-232
9. Fredriksson et al., Nature Biotech (2002), 20: 473-477
10. Fredriksson et al., Nature Methods (2007), 4(4): 327-329
11. Vincent et al., EMBO Reports (2005), 5(8): 795-800
12. Gajadjar et al., Biotechniques (1010), 48(22): 145-152
13. Schallmeiner et al, Nature Methods (2007) 4(2): 135-137
14. Ericsson et al., Nucl. Acids Research (2008), 36(8): e45
15. Darmanis et al., Biotechniques (2007), 43: 443-450
16. Dahl et al., Proc. Natl. Acad. Sci. (2004), 101(13): 4548-4553
17. Weibrecht et al., Expert Rev. Proteomics (2010), 7(3): 401-409
18. Spits et al., Nature Protocols (2005), 1(4): 1965-1970
19. Nordengrahn et al., Vet. Microbio (2008), 127: 227-236
20. Vuoriluoto et al., Mol. Oncology (2011), 5: 105-111
21. Zhang et al., Clinica Chimica Acta (2006), 363: 61-70
22. Andras et al., Mol. Biotech. (2001), 19: 29-44
23. Schweltzer et al., Proc. Natl. Acad. Sci. (2000), 97(18): 10113-10119
24. Jeong, et al., Cell. Mol. Life Sci. (2009), 66: 3325-3336
25. Gill et al., Nucleosides, Nucleotides, and Nucleic Acids (2008), 27: 224-245

26. Gullberg, et al., Current Op. in Biotech. (2003), 14: 82-86
27. Gustafsdottir, et al., Clinical Chemistry (2006), 52(6): 1152-1160
28. U.S. Patent Publication No. 20100075862
29. U.S. Pat. No. 8,222,047
30. U.S. Pat. No. 8,236,574
31. U.S. Pat. No. 8,338,776
32. U.S. Patent Publication No. 20110212537
33. U.S. Patent Publication No. 20120196774
34. U.S. Patent Publication No. 20120289428

The invention claimed is:

1. A method of detecting an analyte of interest in a sample comprising:
   a. contacting the sample with a surface comprising (i) a binding reagent for the analyte, and (ii) an anchoring reagent comprising an anchoring oligonucleotide, and binding the analyte to the binding reagent to form a surface-bound complex;
   b. contacting the surface-bound complex with a first detection reagent for the analyte comprising a first proximity probe and a second detection reagent for the analyte comprising a second proximity probe to form a detection complex comprising the binding reagent, the analyte, and the first and second detection reagents;
   c. contacting the detection complex formed in (b) with one or more connector oligonucleotides comprising: (i) a first connector probe complementary to a first region of the first proximity probe and a first region of the second proximity probe, and (ii) a second connector probe complementary to a second non-overlapping region of the first proximity probe and a second non-overlapping region of the second proximity probe, and ligating the first and second connector probes to form a target oligonucleotide;
   d. amplifying the target oligonucleotide to generate an amplicon comprising (i) a plurality of detection oligonucleotides and (ii) an anchoring oligonucleotide complement, wherein the anchoring oligonucleotide complement is complementary to the anchoring oligonucleotide;
   e. hybridizing the anchoring oligonucleotide to the anchoring oligonucleotide complement;
   f. hybridizing a plurality of detection probes to the plurality of detection oligonucleotides; and
   g. measuring the amount of detection probes bound to the surface, thereby detecting the analyte.

2. The method of claim 1, wherein each of the binding reagent, the first detection reagent, and the second detection reagent comprises an antibody.

3. The method of claim 1, wherein the amplifying comprises PCR (Polymerase Chain Reaction), LCR (Ligase Chain Reaction), SDA (Strand Displacement Amplification), 3SR (Self-Sustained Synthetic Reaction), an isothermal amplification method, or combination thereof.

4. The method of claim 1, wherein the amplifying comprises rolling circle amplification (RCA).

5. The method of claim 1, wherein each detection probe comprises a detectable label, and wherein the measuring comprises measuring the amount of the detectable label.

6. The method of claim 5, wherein the detectable label is capable of being measured by light scattering, optical absorbance, fluorescence, chemiluminescence, electrochemiluminescence (ECL), radioactivity, magnetic field, or combination thereof.

7. The method of claim 6, wherein the detectable label comprises an ECL label.

8. The method of claim 1, wherein the surface comprises a particle.

9. The method of claim 1, wherein the surface comprises a well of a multi-well plate.

10. A method of detecting an analyte of interest in a sample comprising:
   a. contacting the sample with (i) a first detection reagent for the analyte that comprises a first proximity probe, and (ii) a second detection reagent for the analyte that comprises a second proximity probe to form a detection complex;
   b. contacting the detection complex formed in (a) with a surface comprising (i) a binding reagent for the analyte and (ii) an anchoring reagent comprising an anchoring oligonucleotide, thereby forming a surface-bound complex;
   c. contacting the surface-bound complex formed in (b) with one or more connector oligonucleotides comprising: (i) a first connector probe complementary to a first region of the first proximity probe and a first region of the second proximity probe, and (ii) a second connector probe complementary to a second non-overlapping region of the first proximity probe and a second non-overlapping region of the second proximity probe, and ligating the first and second connector probes to form a target oligonucleotide;
   d. amplifying the target oligonucleotide to generate an amplicon comprising (i) a plurality of detection oligonucleotides and (ii) an anchoring oligonucleotide complement, wherein the anchoring oligonucleotide complement is complementary to the anchoring oligonucleotide;
   e. hybridizing the anchoring oligonucleotide to the anchoring oligonucleotide complement;
   f. hybridizing a plurality of detection probes to the plurality of detection oligonucleotides; and
   g. measuring the amount of detection probes bound to the surface, thereby detecting the analyte.

11. The method of claim 10, wherein each of the binding reagent, the first detection reagent, and the second detection reagent comprises an antibody.

12. The method of claim 10, wherein the amplifying comprises PCR (Polymerase Chain Reaction), LCR (Ligase Chain Reaction), SDA (Strand Displacement Amplification), 3SR (Self-Sustained Synthetic Reaction), an isothermal amplification method, or combination thereof.

13. The method of claim 10, wherein the amplifying comprises RCA.

14. The method of claim 10, wherein each detection probe comprises a detectable label, and wherein the measuring comprises measuring the amount of the detectable label.

15. The method of claim 14, wherein the detectable label is capable of being measured by light scattering, optical absorbance, fluorescence, chemiluminescence, electrochemiluminescence (ECL), radioactivity, magnetic field, or combination thereof.

16. The method of claim 15, wherein the detectable label comprises an ECL label.

17. The method of claim 10, wherein the surface comprises a particle.

18. The method of claim 10, wherein the surface comprises a well of a multi-well plate.

19. A method of detecting a plurality of analytes of interest in a sample comprising:
   a. contacting the sample with a surface comprising a plurality of discrete binding domains, each binding domain comprising (i) a binding reagent for an analyte of the plurality of analytes, and (ii) an anchoring reagent comprising an anchoring oligonucleotide, thereby forming a plurality of surface-bound complexes;
   b. contacting each surface-bound complex with: (i) a first detection reagent for the analyte of the surface-bound complex, wherein the first detection reagent comprises a first proximity probe, and (ii) a second detection reagent for the analyte of the surface-bound complex, wherein the second detection reagent comprises a second proximity probe, to form a plurality of detection complexes;
c. contacting each detection complex formed in (b) with one or more connector oligonucleotides comprising: (i) a first connector probe complementary to a first region of the first proximity probe and a first region of the second proximity probe, and (ii) a second connector probe complementary to a second non-overlapping region of the first proximity probe and a second non-overlapping region of the second proximity probe, and ligating the first and second connector probes to form a target oligonucleotide;
d. amplifying the target oligonucleotide of each detection complex to generate a plurality of amplicons, wherein each amplicon comprises (i) a plurality of detection oligonucleotides and (ii) an anchoring oligonucleotide complement, wherein the anchoring oligonucleotide complement is complementary to the anchoring oligonucleotide;
e. hybridizing the anchoring oligonucleotide to the anchoring oligonucleotide complement;
f. hybridizing a plurality of detection probes to the plurality of detection oligonucleotides; and
g. measuring the amount of detection probes bound to the surface, thereby detecting the plurality of analytes.

20. The method of claim 19, wherein each of the binding reagent, the first detection reagent, and the second detection reagent comprises an antibody.

21. The method of claim 19, wherein the amplifying comprises PCR (Polymerase Chain Reaction), LCR (Ligase Chain Reaction), SDA (Strand Displacement Amplification), 3SR (Self-Sustained Synthetic Reaction), an isothermal amplification method, or combination thereof.

22. The method of claim 19, wherein the amplifying comprises RCA.

23. The method of claim 19, wherein each detection probe comprises a detectable label, and wherein the measuring comprises measuring the amount of the detectable label.

24. The method of claim 23, wherein the detectable label is capable of being measured by light scattering, optical absorbance, fluorescence, chemiluminescence, electrochemiluminescence (ECL), radioactivity, magnetic field, or combination thereof.

25. The method of claim 24, wherein the detectable label comprises an ECL label.

26. The method of claim 19, wherein the surface comprises a particle.

27. The method of claim 19, wherein the surface comprises a well of a multi-well plate.

* * * * *